United States Patent [19]

Kaufman

[11] Patent Number: 5,391,351
[45] Date of Patent: Feb. 21, 1995

[54] BODY WASTE FLUIDS SOLIDIFICATION SYSTEM

[76] Inventor: Jack W. Kaufman, 357 Frankel Blvd., Merrick, N.Y. 11566

[21] Appl. No.: 956,582

[22] Filed: Oct. 5, 1992

Related U.S. Application Data

[60] Division of Ser. No. 507,966, Apr. 11, 1990, abandoned, which is a continuation-in-part of Ser. No. 215,370, Jul. 5, 1989, abandoned, which is a continuation-in-part of Ser. No. 105,875, Oct. 7, 1987, abandoned.

[51] Int. Cl.⁶ ................................. A61L 2/16
[52] U.S. Cl. ..................... 422/28; 128/760; 206/219; 206/222; 206/524.7
[58] Field of Search ............ 220/521, 908; 206/219, 206/220, 221, 568, 222, 524.7, 524.6; 422/28, 30, 32; 604/333, 349, 350, 335; 128/760, 751; 428/35.7; 435/296, 299, 300

[56] References Cited

U.S. PATENT DOCUMENTS

| | | | |
|---|---|---|---|
| 2,073,273 | 3/1937 | Wetstein | 206/222 X |
| 3,603,469 | 9/1971 | Magni | 206/47 A |
| 3,690,320 | 9/1972 | Riely | 128/283 |
| 3,797,646 | 3/1974 | Horne | 206/219 |
| 3,870,147 | 3/1975 | Orth | 206/222 |
| 4,002,235 | 1/1977 | Donnelly | 206/219 |
| 4,193,698 | 3/1980 | Gartner | 366/130 |
| 4,195,731 | 4/1980 | Cavazza | 206/222 |
| 4,314,558 | 2/1982 | Korpman | 206/265 |
| 4,315,570 | 2/1982 | Silver et al. | 206/221 |
| 4,615,437 | 10/1986 | Finke et al. | 206/222 |
| 4,853,266 | 8/1989 | Cullen | 421/35.7 |

Primary Examiner—Timothy M. McMahon
Assistant Examiner—Amalia Santiago
Attorney, Agent, or Firm—Lackenbach Siegel Marzullo Aronson & Greenspan

[57] ABSTRACT

A body waste fluid solidification device, comprising a substantially rigid, self standing medical collection vessel, having a rim, for collecting body waste fluids in the medical collection vessel. The lid closes off the rim of the medical collection vessel for sealing same from ambient condition. The device also includes a container of hollowed cylindrical shape having a chamber substantially filled with a hydrophilic xerogel composition with a chamber separating means for separating at least one disinfectant from the hydrophilic xerogel composition. The container is mounted in an opening on the lid, which has a plunger release activated by pressure and dispensing the disinfectant and subsequently the hydrophilic xerogel composition from the container into the medical collection vessel.

31 Claims, 23 Drawing Sheets

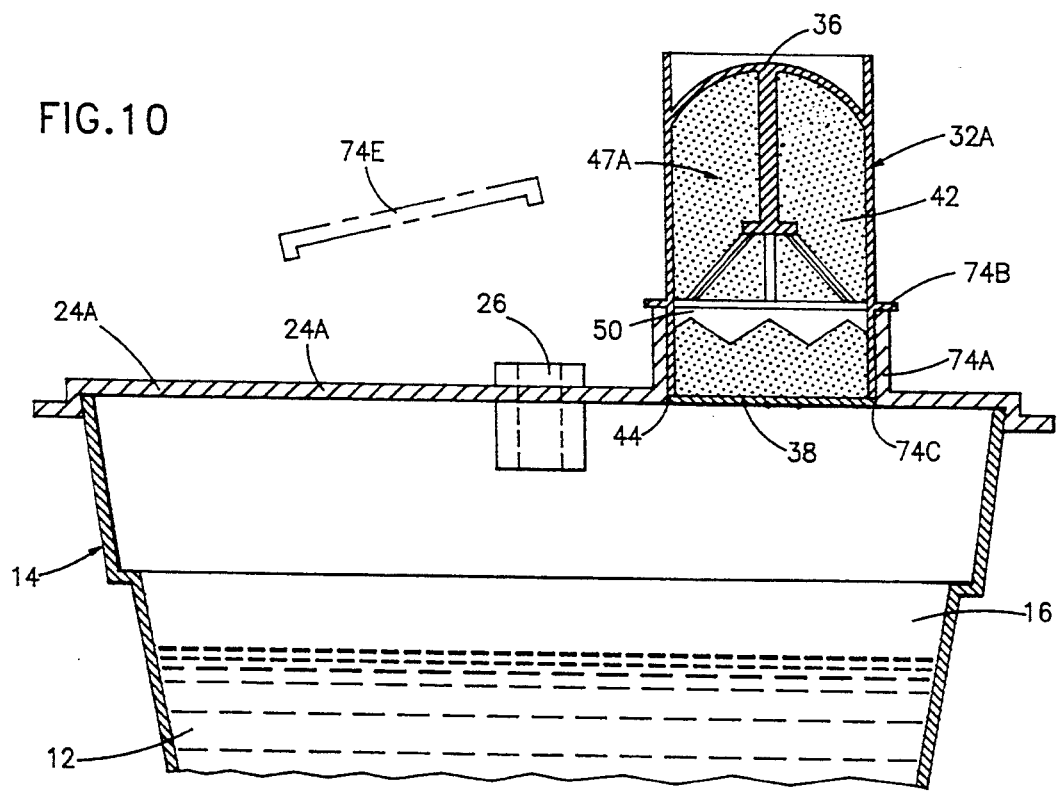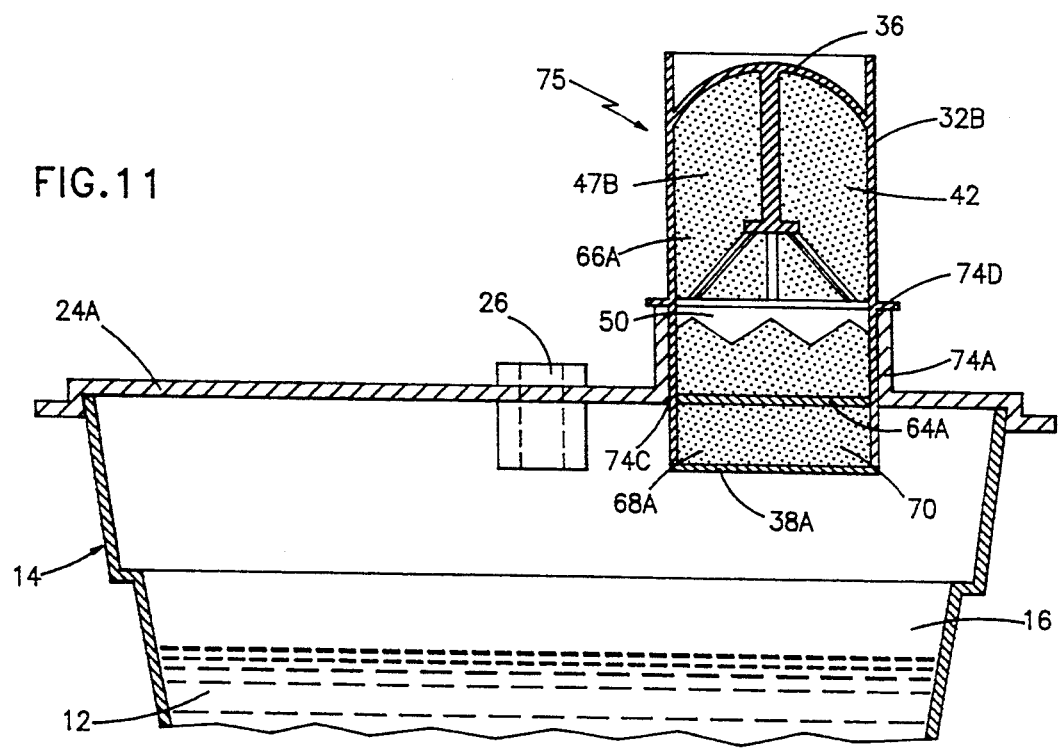

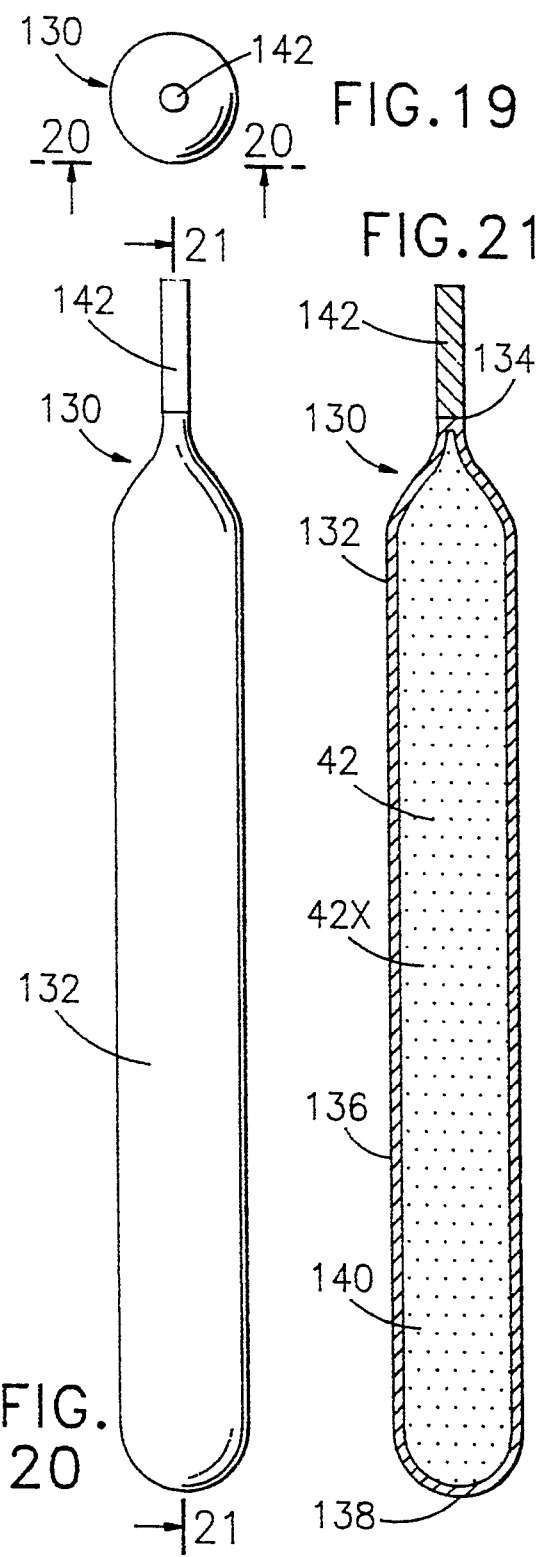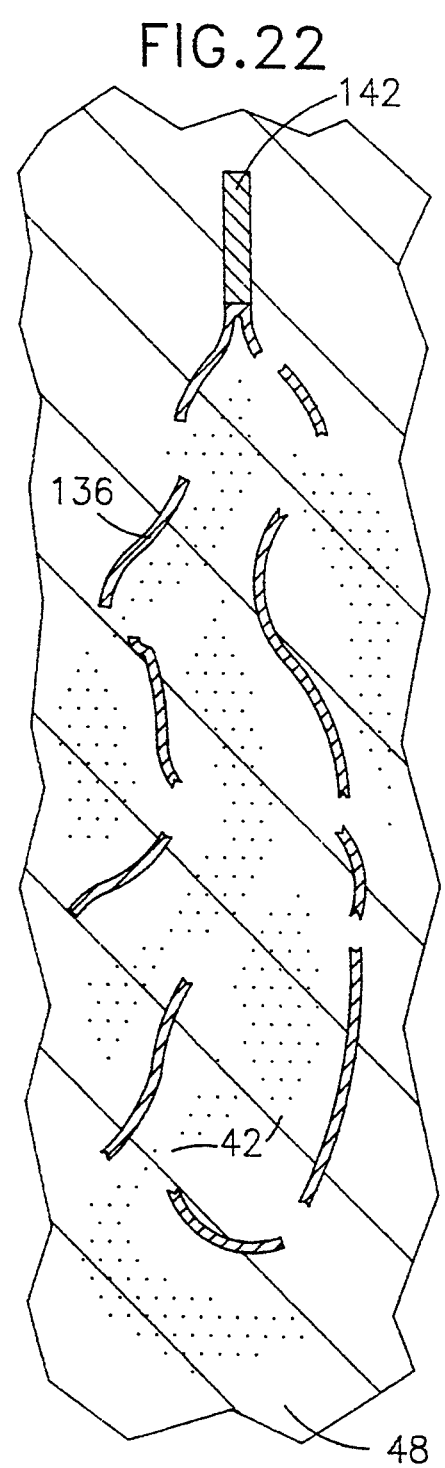

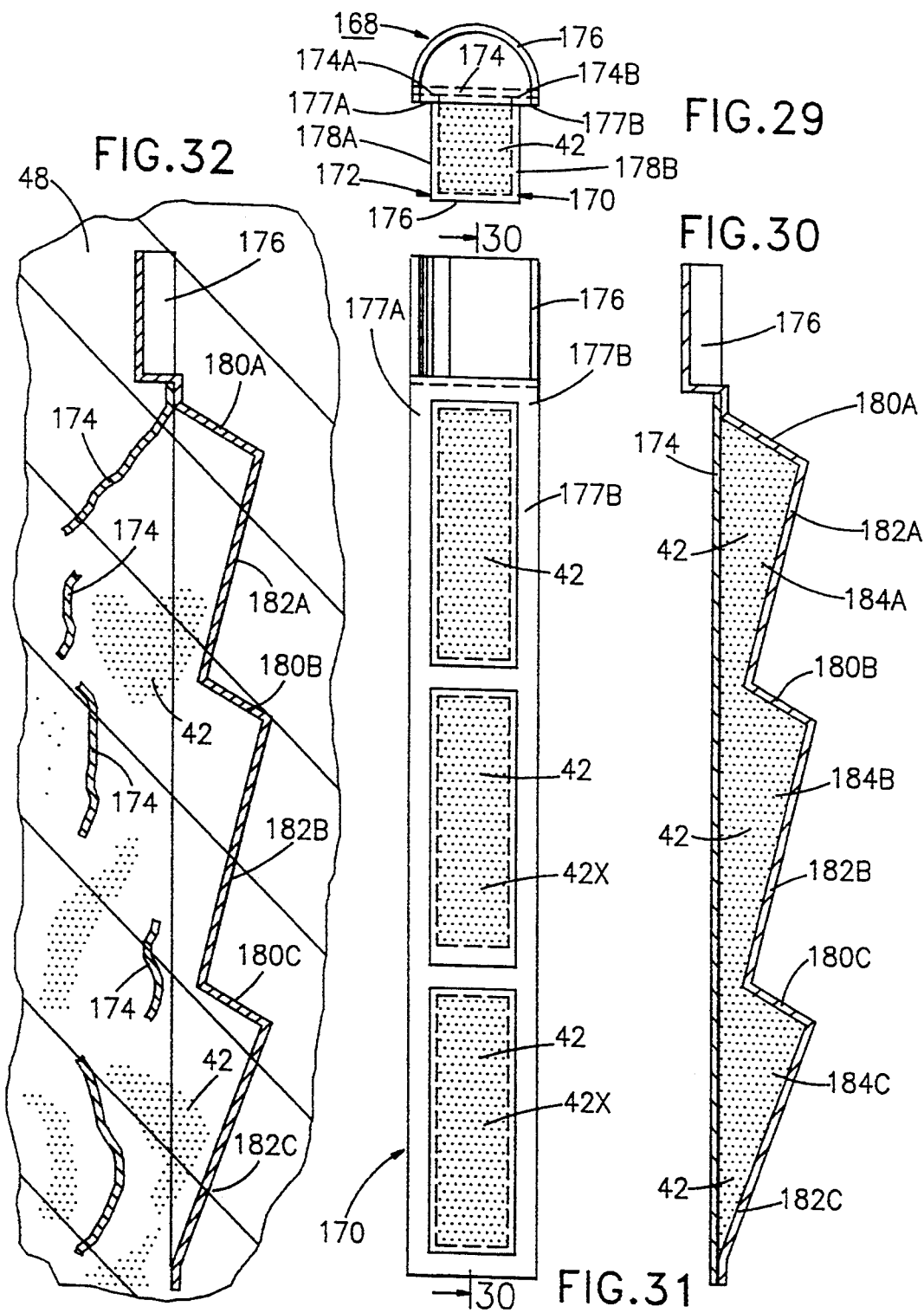

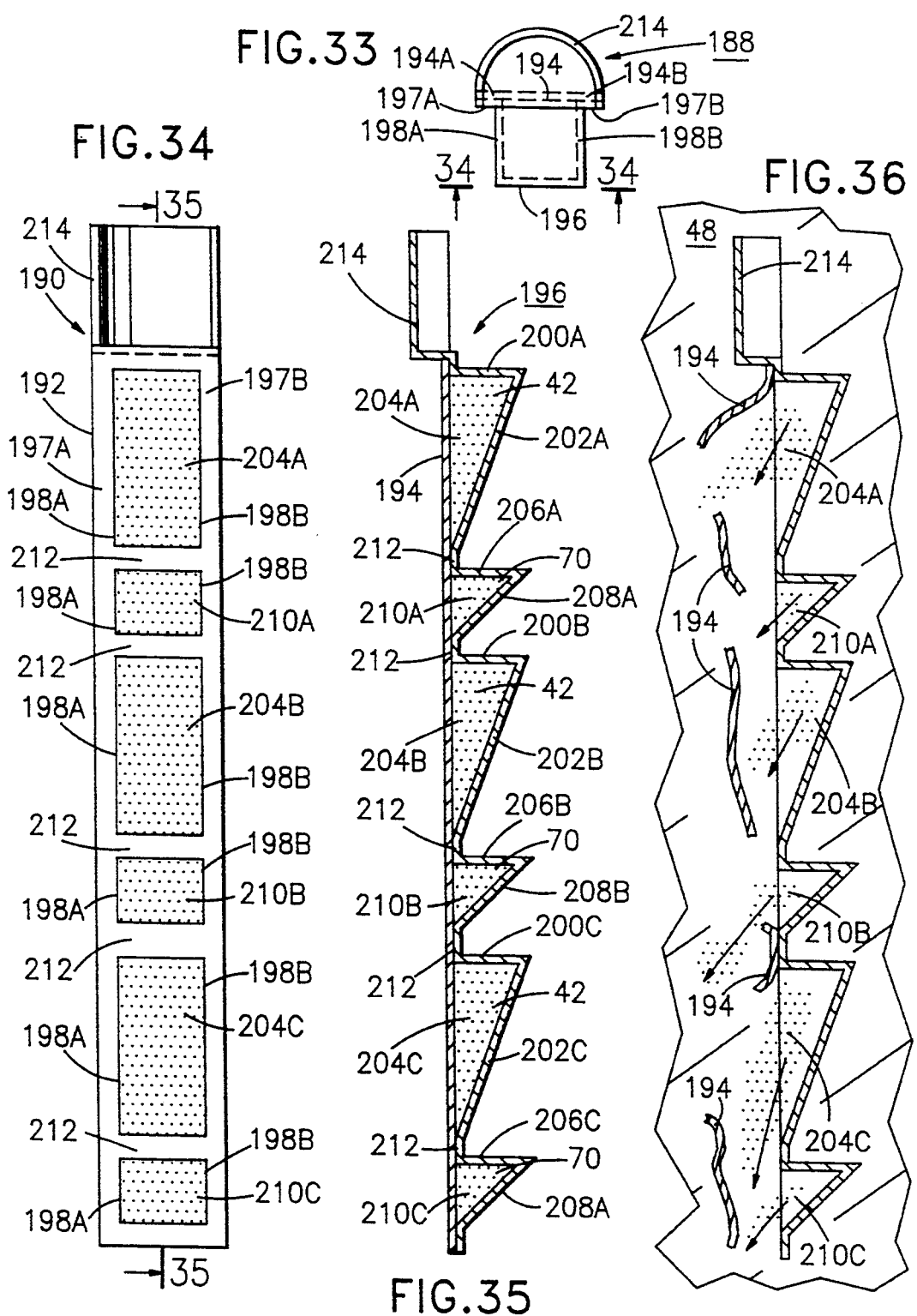

BODY WASTE FLUIDS SOLIDIFICATION SYSTEM

HISTORY OF THE INVENTION

This application is a division of application Ser. No. 507,966, filed on Apr. 11, 1990, which is now abandoned, which in turn is a continuation-in-part of my application Ser. No. 215,370, filed Jul. 5, 1989 (now abandoned), which in turn is a continuation-in-part of my application Ser. No. 105,875, filed Oct. 7, 1987, now abandoned.

FIELD OF THE INVENTION

This invention relates generally to medical waste disposal techniques and more particularly to the preparation for disposal of body waste fluids from patients.

BACKGROUND OF THE INVENTION

Body waste fluids that are drained or drawn from a hospital patient are collected in an operating room or bedside fluid vessel, generally either a rigid-walled canister or a soft-walled plastic fluid vessel that is set into a receptacle mounted to a vacuum machine. Both types of vessels are provided with a lid which has an inlet patient port in turn connected to the patient by a patient line and further has a vacuum port connected to a vacuum machine by a vacuum line. The lid also has a drain port from which the body waste fluids are poured at a designated disposal area in the hospital before disposal of the vessel itself.

When a vessel is carried or otherwise moved from the bedside of the patient, it must be carefully handled because the body waste fluids often contain infectious organisms that are not to come into contact with humans. In addition, the body waste fluids are commonly later emptied from the canister by pouring the contents down a toilet bowl or sink. At the time of pouring, if the waste body fluids hit a hard surface, for example, the side of a toilet bowl, the fluids can aerosolize into the atmosphere and be inhaled by personnel. Another method of disposal of vessels is to carry them to designated disposal areas; any accident during handling of the vessel could result in spilling onto and contamination of the clothing or hands of personnel.

SUMMARY OF THE INVENTION

It is a principal object of this invention to provide a system for preparation for disposal of which solidifies body waste fluids collected in a collection vessel used in hospital rooms and operating rooms in preparation for its disposal.

It is another object of this invention to provide a system for preparation for disposal of body waste fluids collected in a vessel.

It is yet another object of this invention to provide a body waste fluids system which both solidifies body waste fluids in a collection vessel and also destroys or at least deactivates infectious agents within the vessel in preparation for its disposal.

In accordance with the above objects and others which will become apparent hereinafter, there is provided a system for preparation for disposal of non-gaseous body waste fluids collected in a medical collection vessel in a hospital room or operating room. The system includes a container holding at least one hydrophilic xerogel composition in a free-flowing powder form and a release means operatively associated with the container for allowing the xerogel composition to exit from the container into contact with the body waste fluids, whereupon the xerogel composition mixes and interacts with the body waste fluids so as to immobilize the body waste fluids into a solidified mixture, or gel, so that the collection vessel along with the solidified mixture can be efficiently disposed of. The container can optionally also hold a disinfectant powder generally in a compartment separate from the xerogel. The container can be connected to the lid of the collection vessel and the xerogel or the xerogel and the disinfectant allowed to exit the container so as to come into contact with the body waste fluids in the vessel by manual operation of a release system mounted to the container. Another type of container holding the xerogel or the xerogel and the disinfectant can be placed dropped into the collection vessel through the drainage port in the lid of the vessel. The wall of such a container is made of a material such as paper that passes fluid to the xerogel in the container, which expands upon absorption of the fluid and bursts the paper wall so the that xerogel or the xerogel and the disinfectant come into contact with the body waste fluids thus immobilizing them.

Packets of material for absorbing and immobilizing liquid after the liquid comes into contact therewith and the paper are known. One such packet is described in U.S. Pat. No. 4,748,069 issued May 31, 1988 to Cullen.

The present invention will be better understood and the objects and important features, other than those specifically set forth above, will become apparent when consideration is given to the following details and description, which when taken in conjunction with the annexed drawings, describes, discloses, illustrates and shows preferred embodiments or modifications of the present invention and what is presently considered and believed to be the best mode of practice in the principles thereof. Other embodiments or modifications may be suggested to those having the benefit of the teachings herein, and such other embodiments or modifications are intended to be reserved especially as they fall within the scope and spirit of the subjoined claims.

BRIEF DESCRIPTION OF THE DRAWINGS

FIG. 10 is a partial sectional view similar to the view of FIG. 9 with the independent container having been fully inserted into the drain port with the release device in an inactive mode;

FIG. 11 is a partial sectional view similar to the view shown in FIG. 6 showing a modified embodiment of FIG. 9 with a container holding both xerogel composition and germicide powder having been mounted to the canister by manual insertion through the drain port with the release device in an inactive mode;

FIG. 19 is a top view of another embodiment of a body waste solidification system having an elongated container holding a xerogel powder;

FIG. 20 is an elevational view taken through line 20—20 of FIG. 19;

FIG. 21 is a sectional view taken through line 21—21 of FIG. 20;

FIG. 22 is a partial sectional side view of the elongated container having been inserted through the drain port of the canister lid shown in FIG. 20 into the storage volume and the body waste fluids therein;

FIG. 29 is a top view of another of a body waste fluids solidification system including an elongated container holding a xerogel powder;

FIG. 30 is a frontal elevational view taken through line 30—30 in FIG. 29;

FIG. 31 is a sectional side view taken through line 31—31 in FIG. 30;

FIG. 32 is a sectional side view analogous to the side view of FIG. 31 with the container having been placed in a canister with the xerogel powder escaping from the container;

FIG. 33 is a top view of another of a body waste fluids solidification system analogous to the system shown in FIGS. 29-32 with compartments for both a xerogel composition and a disinfectant powder;

FIG. 34 is a frontal view taken through line 33—33 of FIG. 33;

FIG. 35 is a sectional view taken through line 35—35 in FIG. 34;

FIG. 36 is a sectional side view analogous to the sectional view of FIG. 35 with the container having been placed in a canister with the xerogel powder escaping from the container;

DESCRIPTION OF THE PREFERRED EMBODIMENTS

Figure 1:
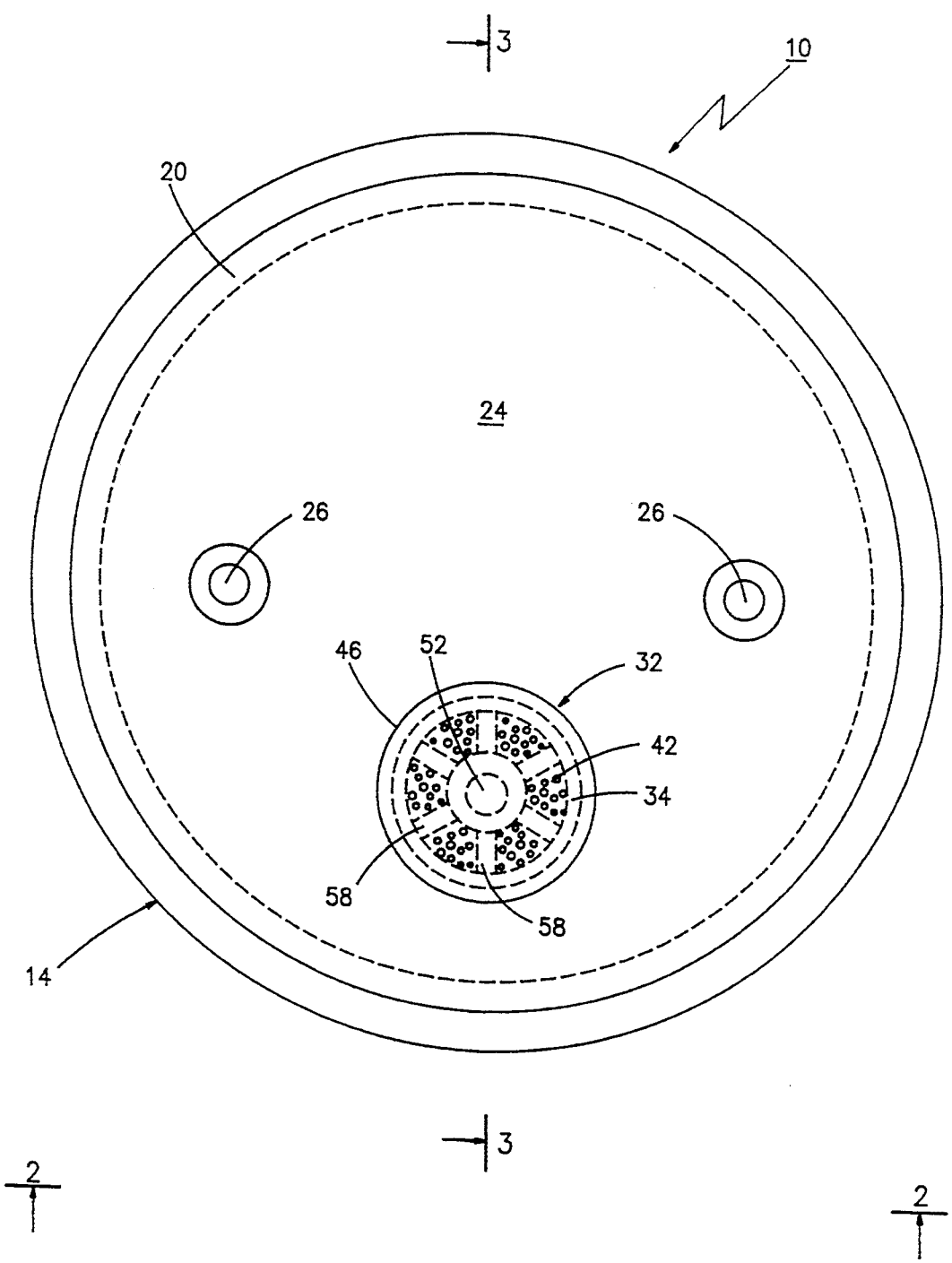
FIG. 1 is a top view of a rigid-walled canister and canister lid including a body waste solidification system.

A detailed description of the preferred embodiments based upon the above-named figures is set forth below with the same numerals indicating the same or similar elements throughout the figures.

A system 10 for preparation for disposal of non-gaseous body waste fluids 12 collected in a medical waste fluids vessel, or canister, 14 illustrated in FIGS. 1–4 which defines a storage volume 16 which holds body waste fluids 12. Canister 14 has a generally cylindrical upright wall 20 and a bottom wall 22 which together define storage volume 16. A canister lid 24 is removably secured to canister 14 at the top edge of cylindrical wall 20. Canister 14 and canister lid 24 are made of a rigid plastic material. Canister lid 24 has a patient inlet port 26 in turn connected to the patient by a patient line and a vacuum port 28 connected to a vacuum line. Canister lid 24 is provided with an aperture 30 opening.

A container 32 sealably positioned in aperture 30 by a sealing ring 35 includes a continuous generally upright wall 34 and opposed upper and lower walls 36 and 38, respectively, transverse to cylindrical wall 34 that together define a sealed chamber 40 configured as a cylinder having a generally vertical axis holding at least one hydrophilic xerogel composition 42 in powder form, the powder being a free-flowing powder. Xerogel 42 includes at least one hydrophilic polymer. Chamber 42 has an exit port 44 with lower wall 38 being removably mounted, for example, by gluing to cylindrical wall 34 at exit port 44. Lower wall 38 is a thin, penetrable material such as foil. Container 32 includes a top portion with cylindrical side wall 34 extending above domed upper wall 36 terminating in a top edge 45. A removable cap 46 is positioned around top edge 45.

Figure 4:
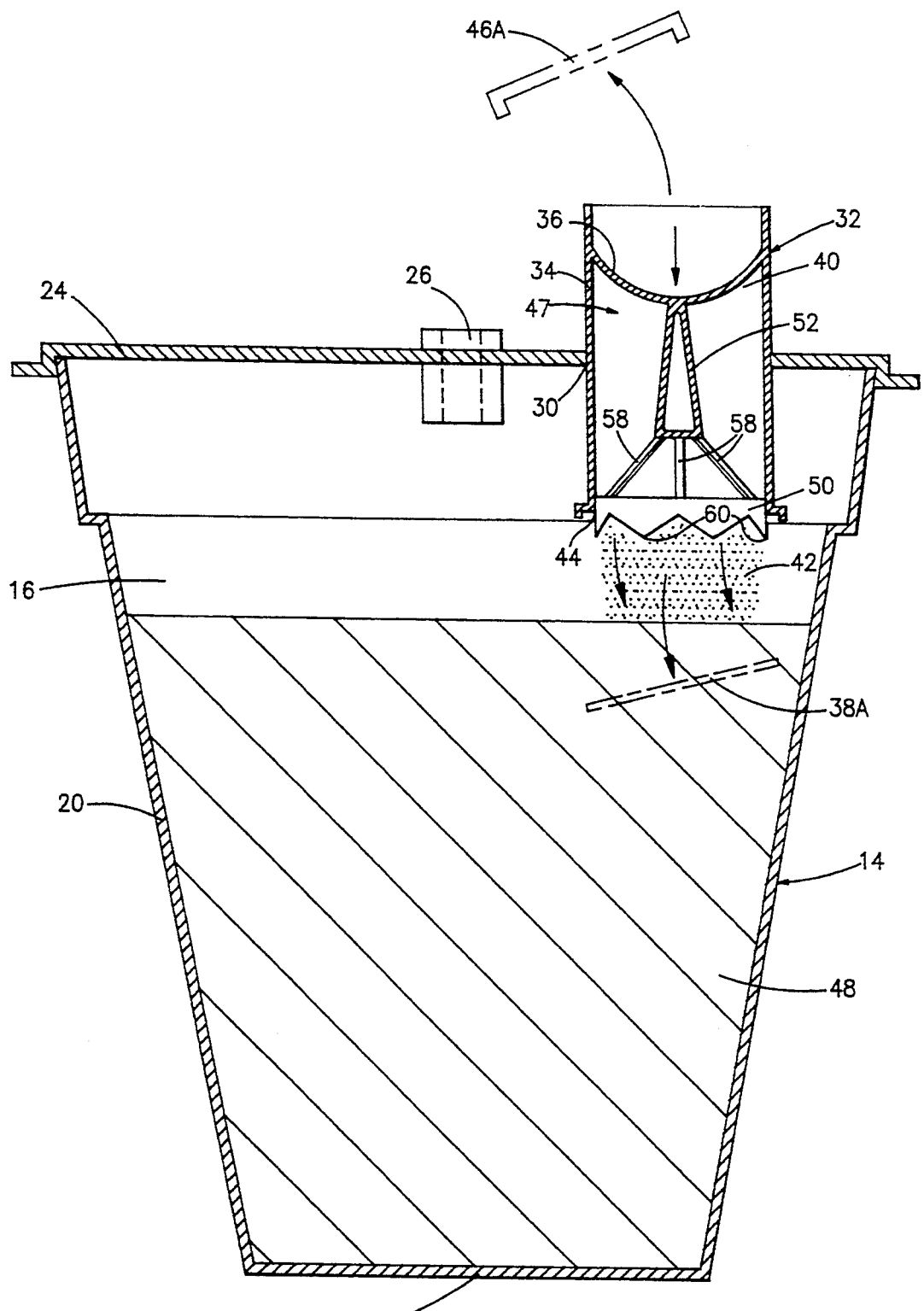
FIG. 4 is a sectional view analogous to the sectional view of FIG. 3 with the release device of the xerogel container in an activated mode with the xerogel powder emptied into the body waste fluids shown having been immobilized from its former fluid state to a solidified mixture.
Figure 5:
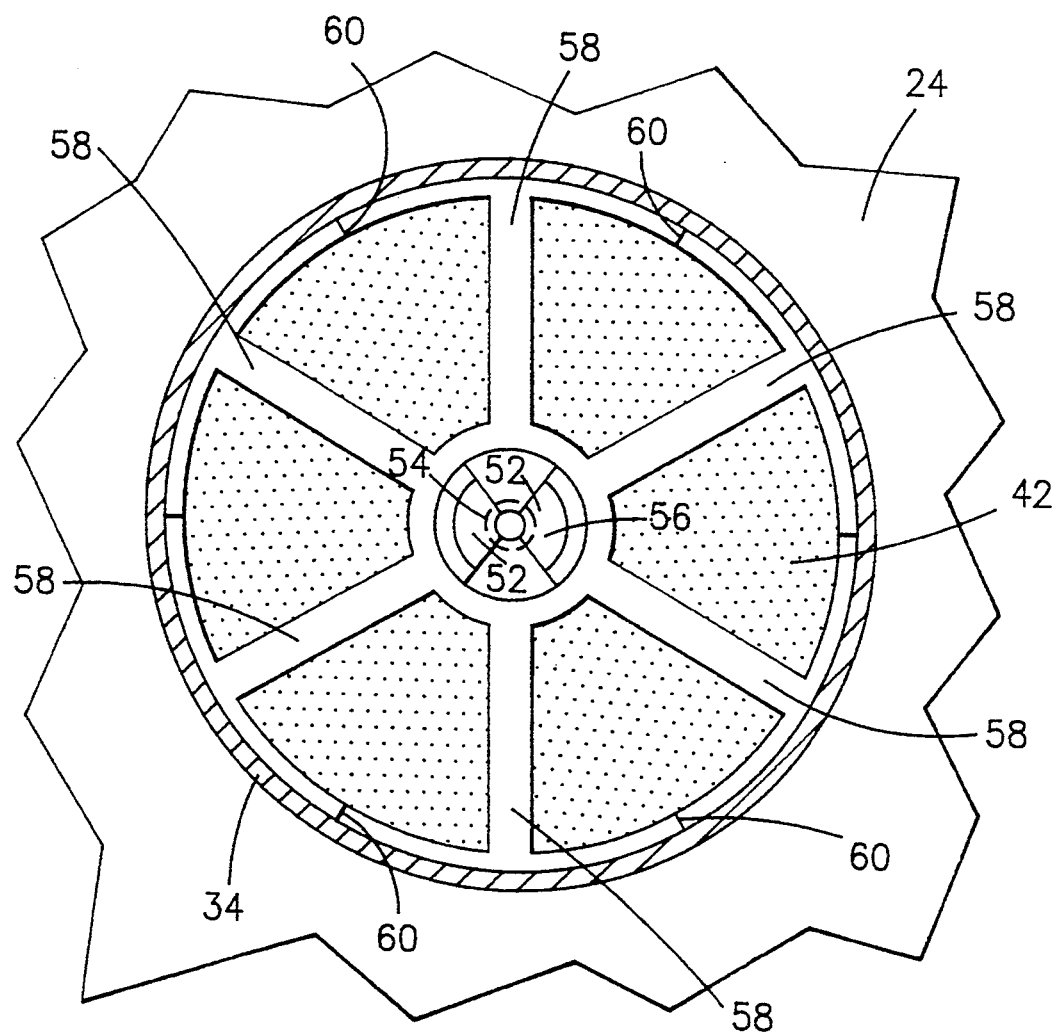
FIG. 5 is a bottom sectional view of the xerogel container taken through line 5—5 of FIG. 2.

A release device 47 operatively associated with container 32 allows xerogel composition 42 to exit, or outflow, by force of gravity from chamber 40 into contact with body waste fluids 12. When xerogel composition 42 mixes with body waste fluids 12, xerogel composition 42 interacts with body waste fluids 12 so that xerogel composition 42 absorbs the aqueous portion of body waste fluids 12 resulting in an insoluble gel in which the remainder of the fluids are absorbed and immobilized resulting in a solidified mixture 48 as illustrated in FIG. 4.

Figure 2:
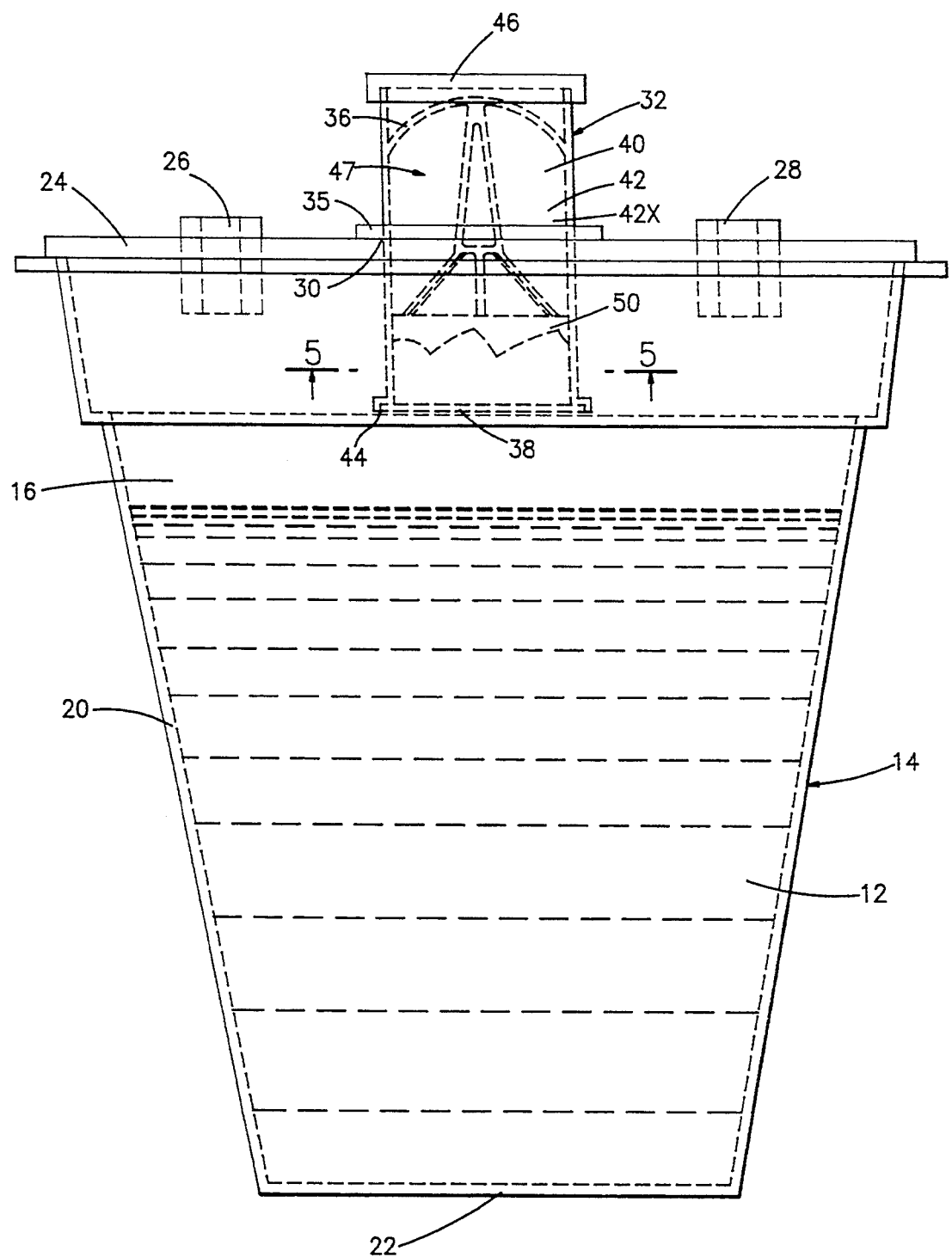
FIG. 2 is an elevational view taken through line 2—2 in FIG. 1 which illustrates a xerogel container integral with the canister lid and which holds a xerogel powder.
Figure 3:
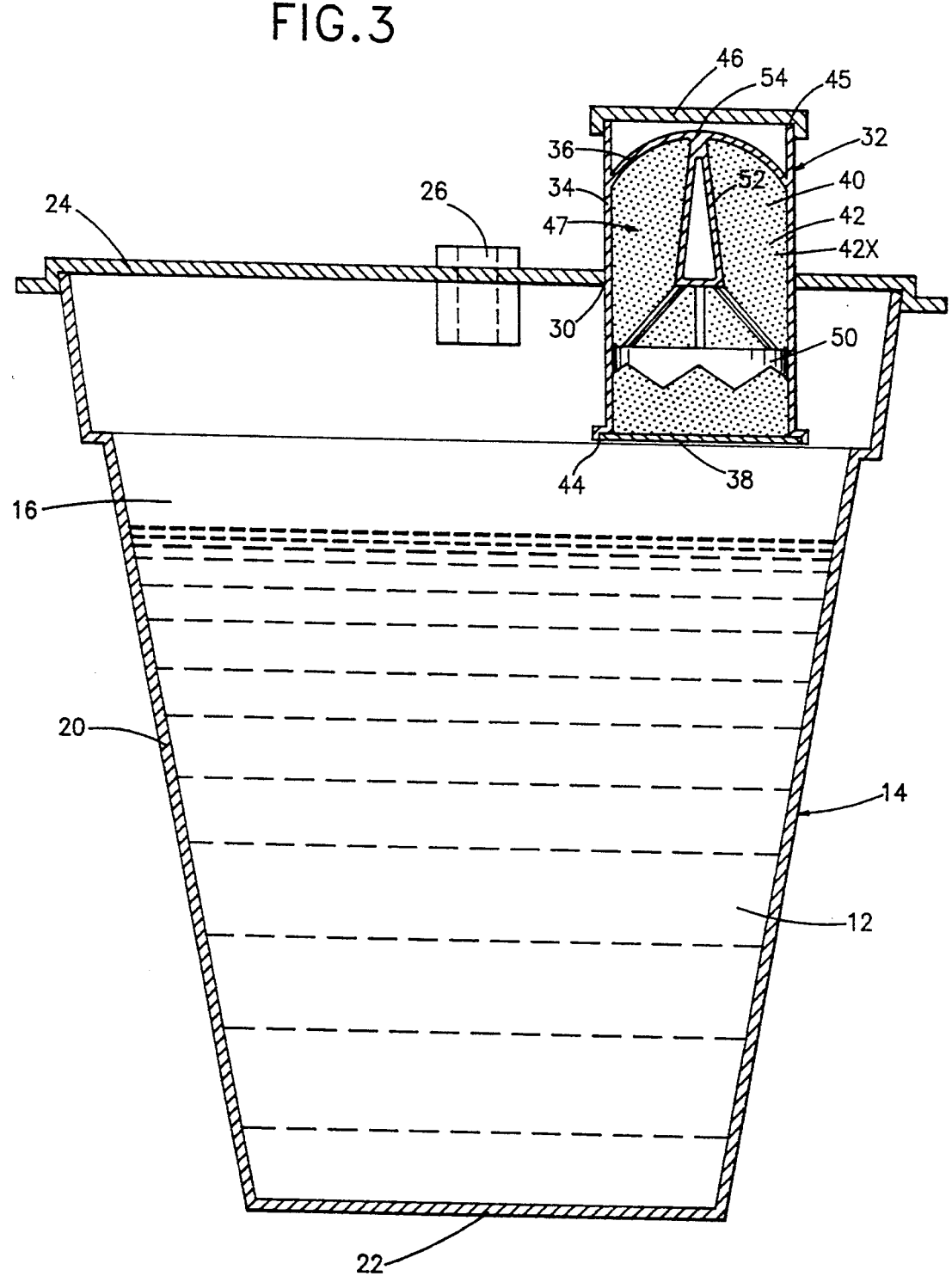
FIG. 3 is a sectional view taken through line 3—3 of FIG. 1 showing the xerogel container with the xerogel powder therein and the release device in a inactive mode.

Release device 47 includes a punch head 50 slidably mounted in chamber 40 and a generally vertical connecting connecting rod 52 positioned at the axis of chamber 40 and having upper and lower ends 54 and 56, respectively, upper end 54 being flexibly connected to the axial center of domed upper wall 36. Rod 52 is configured as a pair of semi-cylindrical walls spaced slightly apart but can optionally be a single straight piece. Upper wall 36 is domed, or dome-shaped, and is integrally and flexibly connected around its circular peripheral edge to the inner surface of cylindrical wall 34. Domed upper wall 36, connecting rod 52, and punch head 50 are movable by exertion of downward manual pressure against upper wall 36, after removal of cap 46, from an inactive position as illustrated in FIGS. 2 and 3 to an activated position as illustrated in FIG. 4. Domed upper wall 36 is convex upwardly in the inactive position and is convex downwardly in the activated position. The inactive position is when punch head 50 is spaced above removable lower wall 38, and the activated position is when punch head 50 is positioned below exit port 44 after having punched removable lower wall 38 from connection with container 32 and into storage volume 16 of canister 14 at which time xerogel composition 42 is released from chamber 40 for movement into storage volume 16 for mixture therein with body waste fluids 12 resulting in the formation of gel 48.

Punch head 50 is configured as an interior cylindrical wall slidably mounted within and axially aligned with cylindrical chamber 40. Connecting rod 52 includes six equally spaced support rods 58 extending downwardly at an angle between lower end 56 of connecting rod 52 and punch head 50. Container 32, domed upper wall 36, support rods 58, punch head 50, and connecting rod 52 are integral and made of a flexible plastic to allow hinged movements between the top of connecting rod 52 and domed upper wall 50 and between the circumference of domed upper wall 36 and the interior of container 32. Chamber 40 holding xerogel composition powder 42 includes areas above and below support rods 58. When punch head 50 is moved to the activated position, the portion of xerogel composition 42 positioned in chamber 40 above punch head 50 passes downwardly between support rods 58 as the portion of xerogel composition 32 exits downwardly through exit port 44.

Removable lower wall 38 is configured as a flat cylinder and is made of a penetrable material such as foil. Punch head 50 includes a plurality of downwardly directed piercing tips 60 located around the bottom side of the interior cylindrical wall of punch head 50, wherein when punch head 50 is moved from the inactive position to the activated position, piercing tips 60 penetrate lower wall 38 so as to aid in the removal of lower wall 38 from sealable connection with container 32 by the downward force from punch head 50.

Release device 47 is analogous to a release device for a men's hair colorant manufactured by the Clairol Corporation.

Figure 6:
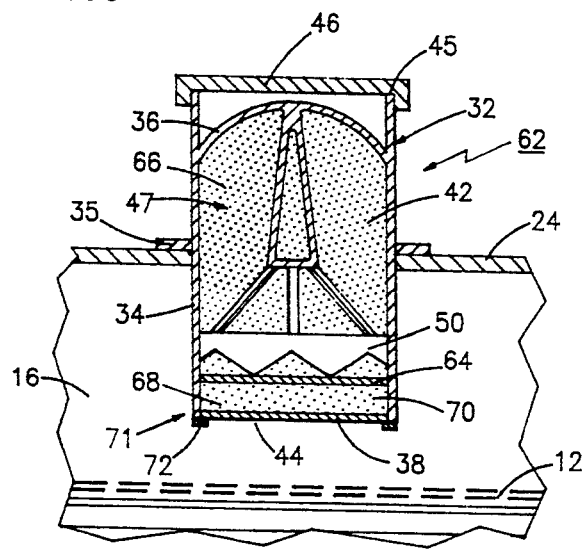
FIG. 6 is a partial sectional view of a variation of the embodiment shown in FIG. 3 with the xerogel container holding both a xerogel powder and a disinfectant powder with the system shown in an inactive mode.
Figures 7, 8:
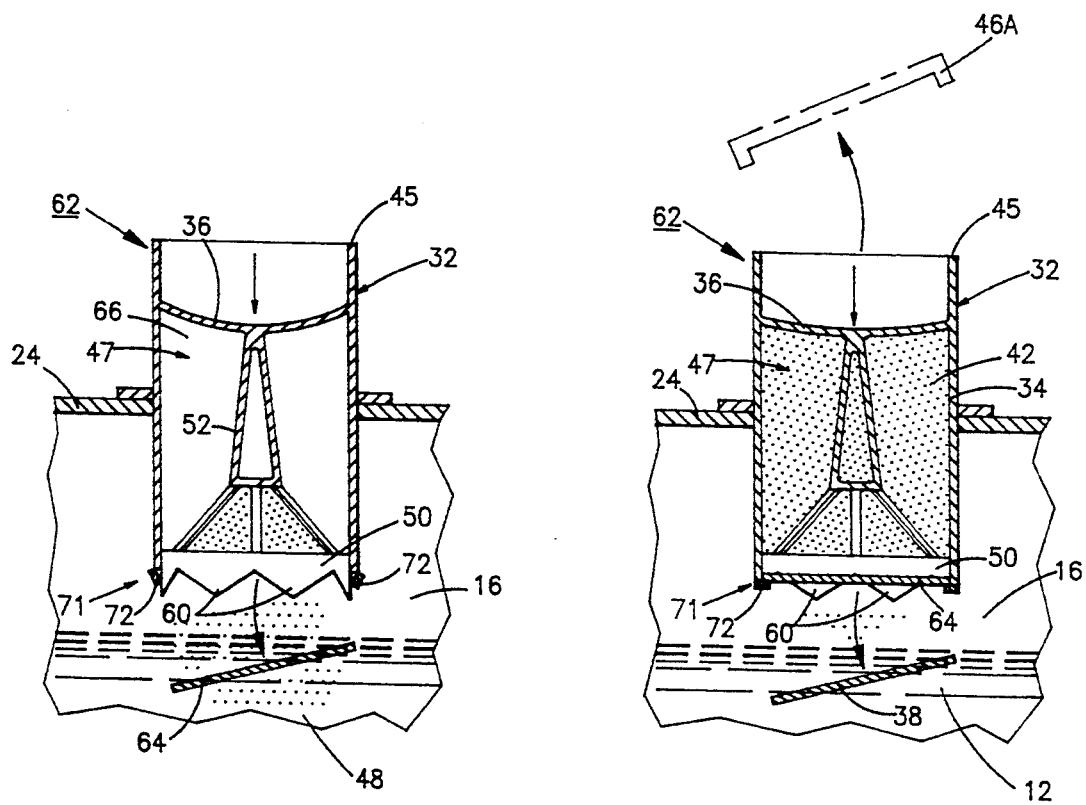
FIG. 7 is a partial sectional view of the embodiment shown in FIG. 6 with the system shown in a partially activated mode.
FIG. 8 is a partial sectional view of the embodiment shown in FIGS. 6 and 7 with the system shown in a fully activated mode.

FIGS. 6, 7, and 8 illustrate a system 62 analogous to system 10 with a container 32A likewise mounted to a canister 14 having a canister lid 24A and an aperture 30A analogous to container 32, lid 24, and aperture 30 described above in relation to system 10. A release device 47A analogous to release device 47 of system 10 is mounted to container 32A. A removable intermediate sealing wall 64 which when system 62 is in an inactive position is located within chamber 40 between and lateral to upper and lower chamber walls 36 and 38 forming from chamber 40 upper and lower compartments 66 and 68, respectively, wherein upper compartment 66 contains xerogel powder composition 42, and lower compartment 68 contains a disinfectant 70 in the form of a powder, the powder being a free-flowing powder.

Domed upper wall 36, connecting rod 52, and punch head 50 are movable by exertion of downward manual pressure against upper wall 36, after removal of cap 46, from an inactive position as illustrated in FIG. 6 to an activated position as illustrated in FIG. 4 to a semiactivated position as illustrated in FIG. 7 and then movable to the fully activated position as illustrated in FIG. 8. The inactive position is when punch head 50 is located above exit port 44. The semiactivated position is when said punch head 50 is positioned immediately above exit port 44 after having caused removable lower wall 38 to be moved from connection with container 32 via manual pressure applied to punch head 50 causing intermediate wall 64 to be moved to exit port 44, so that disinfectant 70 is released from lower compartment 68 for movement into storage volume 16 of canister 14 for mixture therein with body waste fluids 12 resulting in the substantial destruction or at least deactivation of infectious agents in body waste fluids 12 in storage volume 16. The fully activated position is when punch head 50 has been moved downwardly by further manual pressure at upper wall 36 for positioning below exit port 44 after having punched intermediate wall 64 from connection with container 32 into storage volume 16 of canister 14, so that xerogel composition 42 is released from upper compartment 66 into storage volume 16 of canister 14 for mixture therein with the now sterilized body waste fluids 12 resulting in the formation of a solidified mixture, or gel, in storage volume 16.

A locking device 71 connected to container 32 at exit port 44 for holding lower wall 38 in position when system 62 is in the inactive position and is also for holding intermediate wall 64 in position at exit 44 when system 62 is in the semiactivated position. Locking device 71 includes a resilient, or biasable, ring 72 secured around the circumference of exit port 44 and extending radially inwardly so as to provide a circular support upon which is positioned lower wall 38 or intermediate wall 64 in the inactive or semiactivated positions. Biasable ring 72 flexes downwardly when sufficient pressure is placed upon it during the downward movement of release device 47 so as to release lower wall 38 from recess 78 after which release intermediate wall 64 continues to move downwardly until resistance is met by biasable ring 72 at which time the manual pressure is lifted briefly until disinfectant 70 has time to mix with body waste fluids 12 after which the system is manually moved to the fully activated position so that intermediate wall 64 is pressured downwardly so as to cause biasable ring 72 to flex downwardly sufficiently for intermediate ring 64 to pass into into storage volume 16 and release of xerogel composition 42 into storage volume 14 for mixing with sterilized body waste fluids 12 resulting in the subsequent formation of sterilized solidified mixture or gel 48.

Figure 9:
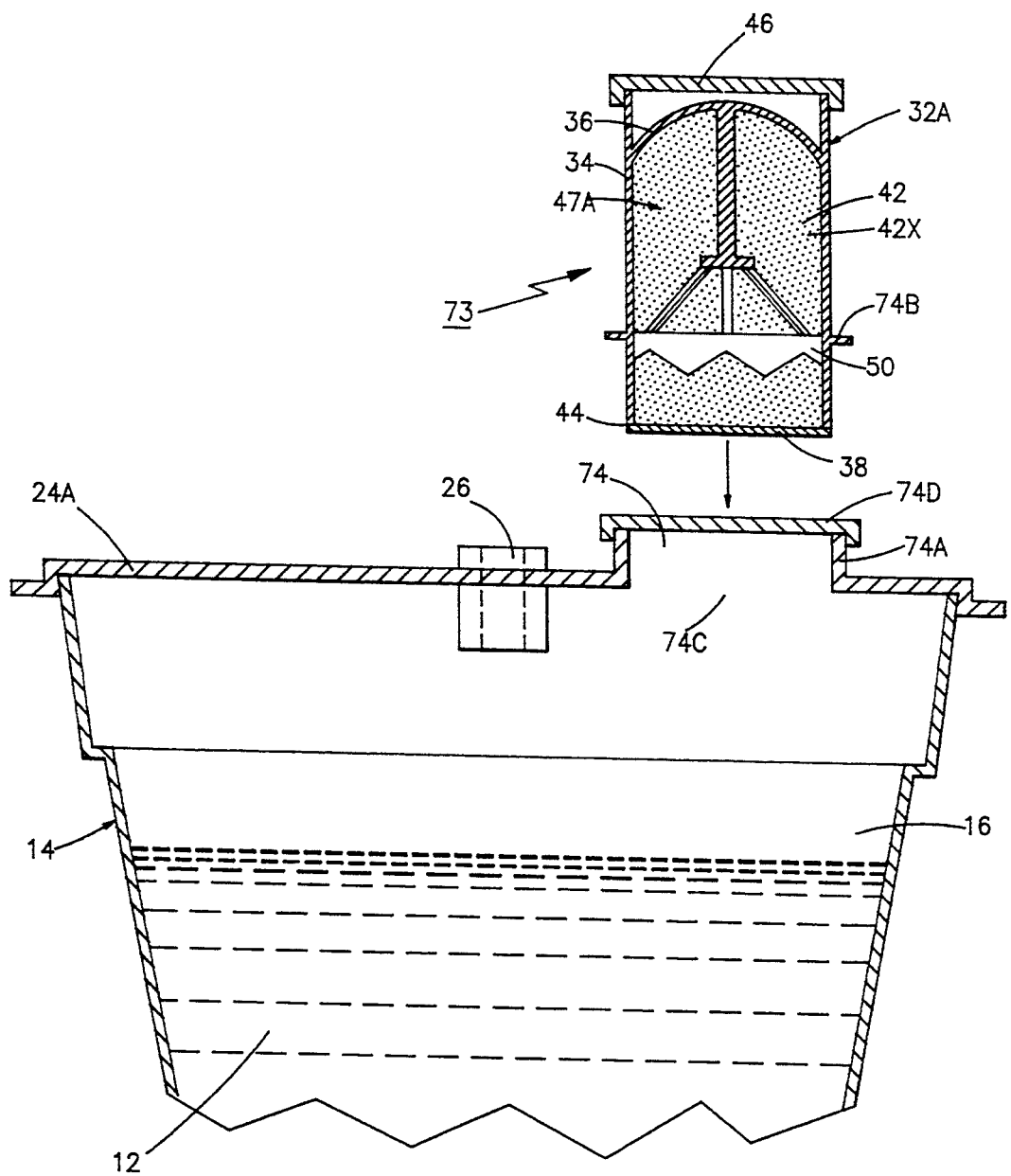
FIG. 9 is a partial sectional view analogous to the view shown in FIG. 3 of another embodiment of the invention with an independent container holding xerogel composition in position to be mounted to the canister through the drain port in the canister lid.
Figure 12:
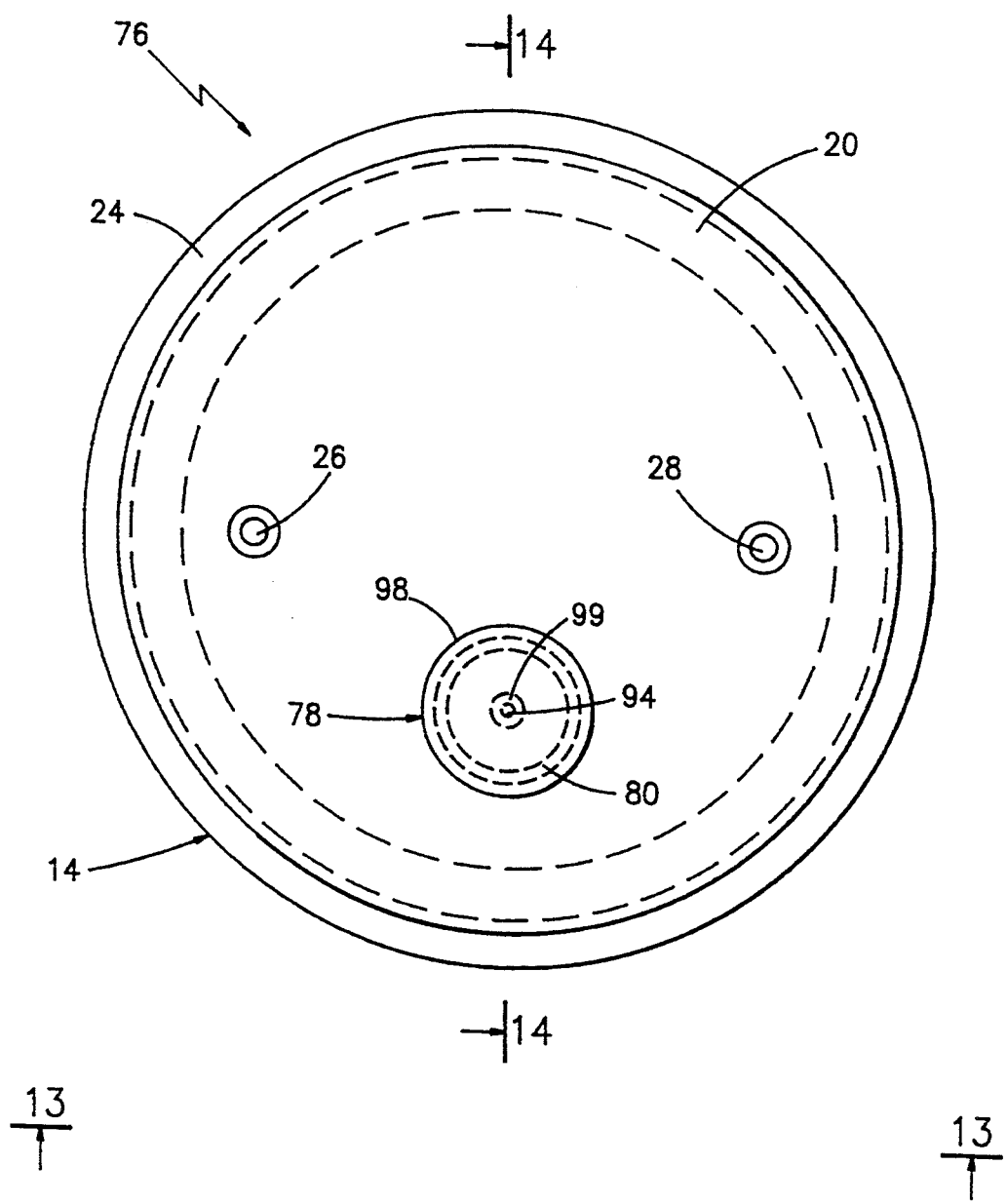
FIG. 12 is a top view of a canister and canister lid including another embodiment of a body waste solidification system.
Figure 13:
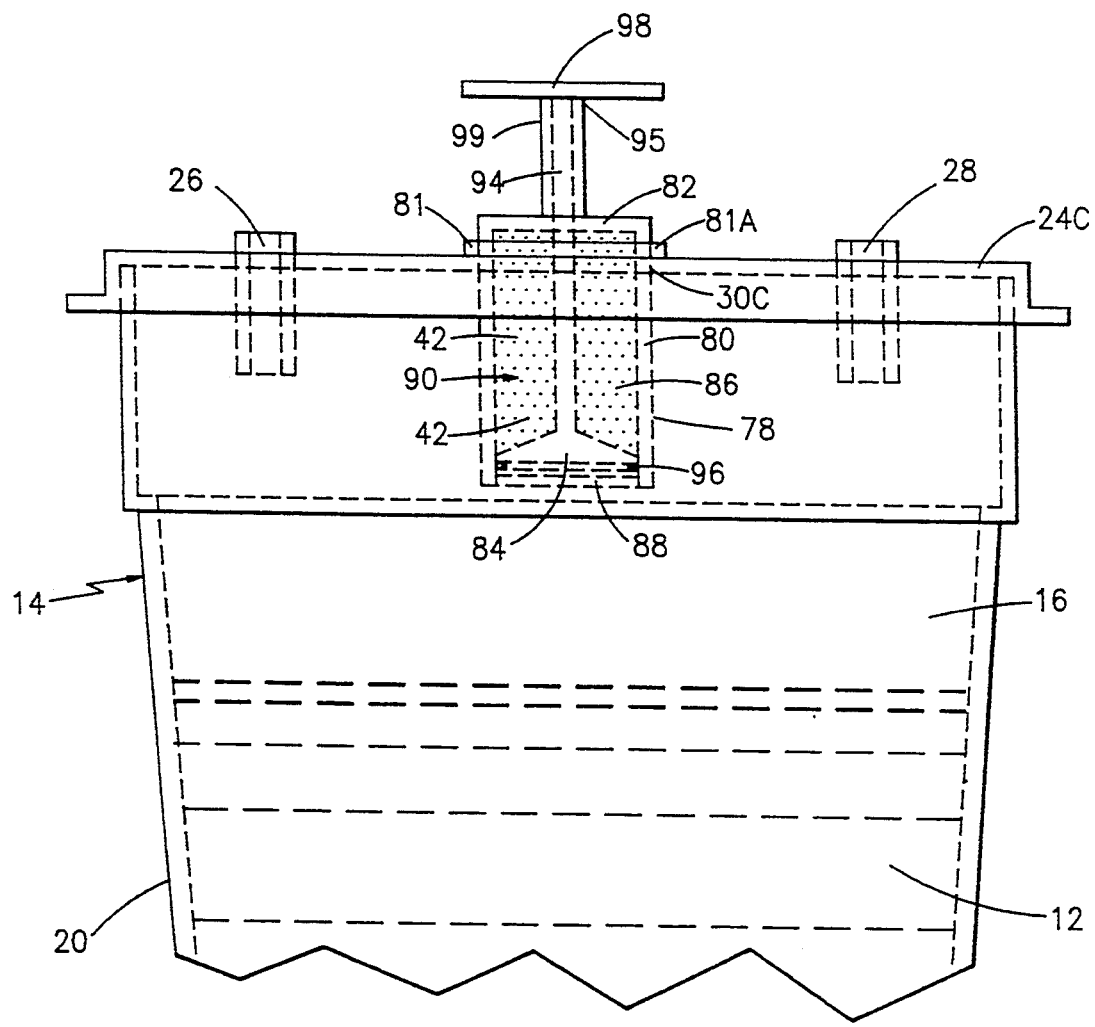
FIG. 13 is an elevational view taken through line 13—13 in FIG. 12 which illustrates a xerogel container integral with the canister lid and which holds a xerogel powder.
Figure 14:
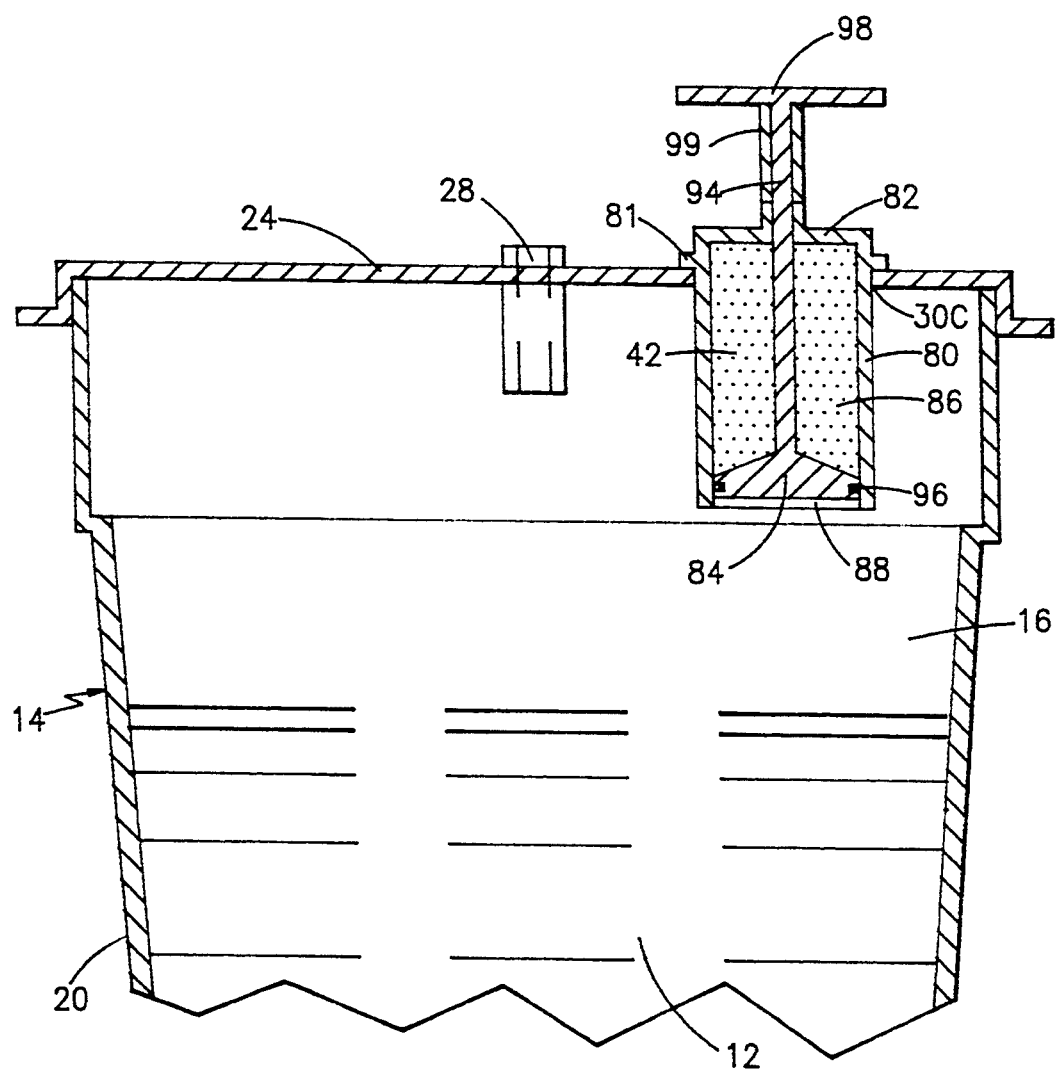
FIG. 14 is a sectional view taken through line 14—14 of FIG. 12 with the plunger in an inactive mode.
Figure 15:
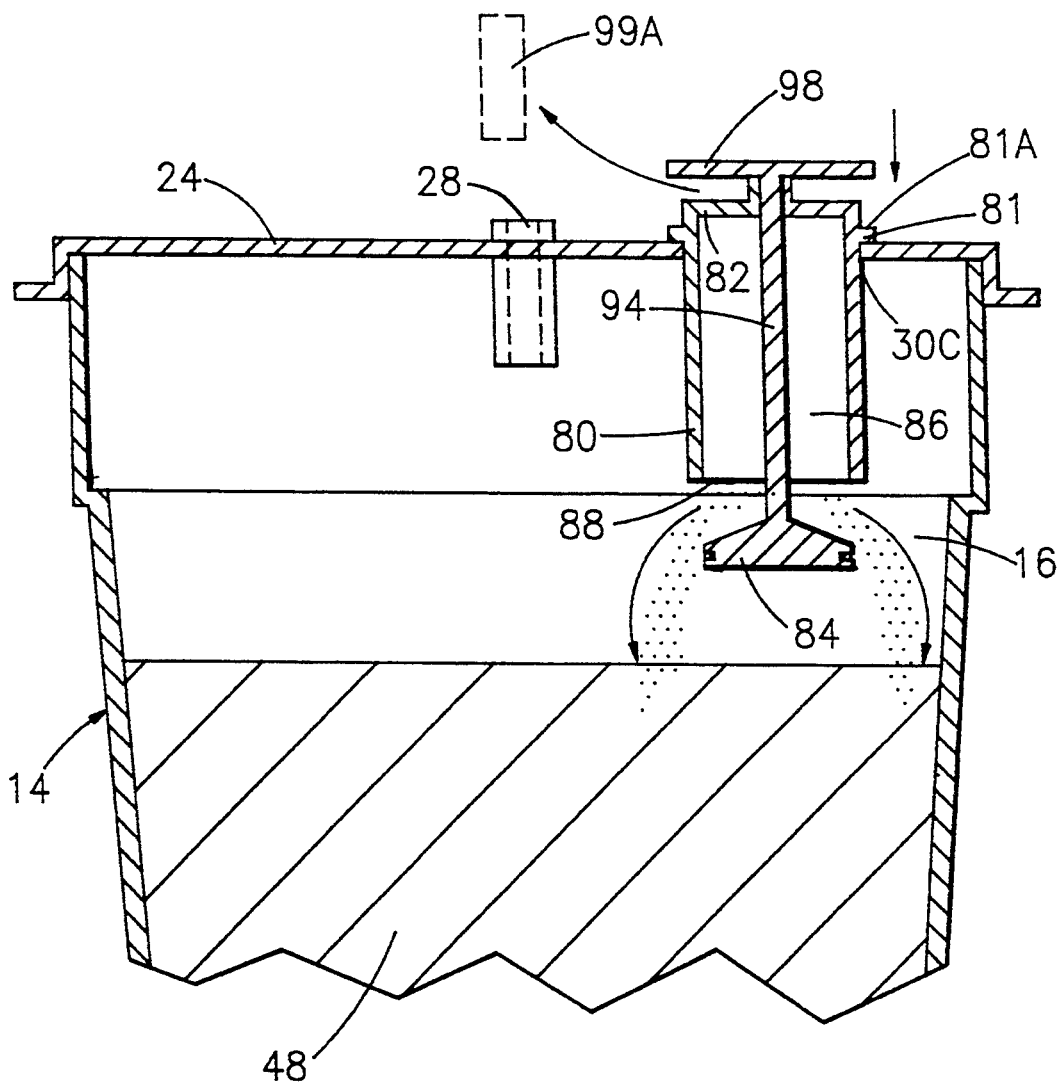
FIG. 15 is a sectional view analogous to FIG. 14 with the plunger in an activated mode.

Another body waste fluids solidification system 73 analogous to system 10 is illustrated in FIGS. 9 and 10, which in turn is analogous in cross-section to FIGS. 3 and 4. Canister 14 has a canister lid 24A which has a drain port 74 which is of the type of canister lid in current use. An independent container 32A having a cylindrical wall 34A holds xerogel composition 42 and is provided with a release device 47A the same as release device 47 provided for system 10. Independent container 32A is separate and apart from canister lid 24A but otherwise mutatis mutandis is like container 32 of system 10. FIG. 9 illustrates independent container 32A positioned for insertion into canister 14 through pre-existing drain port 74 having an upright cylindrical wall 74A. The diameter of container 32A is slightly less than the diameter of drain port 74. A cylindrical stop ring 74B is flanged outwardly from container wall 34A. Insertion of container 32A into drain port 74 after removal of drainage port cap 74D, shown in FIG. 10 in phantom line in the removed position as cap 74E, takes place after body waste fluids 12 have accumulated in storage volume 16. FIG. 10 illustrates independent container 32A positioned in drainage port 74 in a mounted position with canister lid 24A with stop ring 74B settled against port wall 74A ready for manual operation from the inactive position as shown and described relative to the activated position illustrated in FIG. 3 and in FIG. 4, respectively. Exit port 44 of container 32A is aligned with the aperture 74C of drainage port 74 opening to storage volume 16 of canister 14. Cylindrical wall 34A is optionally tapered inwardly so as to be adapted for a press fit, that is, a friction fit with drainage port wall 74A.

Another body waste fluids solidification system 75 analogous to system 62 of FIG. 6 is illustrated in FIG. 11. Canister 14 has a canister lid 24A the same as canister lid 24A as hereinabove described in relation to FIGS. 9 and 10. An independent container 32B holds xerogel composition 42 in an upper compartment 66A and disinfectant 70 in a lower compartment 68A is provided with a release device 47B the same as release device 47A of system 62. An intermediate sealing wall 64A separate upper and lower compartments 66A and 68A and a removable lower wall 38A is removably secured to to the exit port of container 36B. Independent container 32B is separate and apart from canister lid 24A but otherwise mutatis mutandis is like container 32A of system 62. FIG. 11 illustrates independent container 32B having been inserted into canister 14 through pre-existing drain port 74 of canister lid 24B ready for manual operation from the inactive position as shown in FIG. 6 to the semiactivated and activated positions as shown in FIGS. 7 and 8, respectively. The diameter of container 32B is slightly less than the diameter of drain port 74. Insertion takes place after the body waste fluids 12 have accumulated in storage volume 16. Container 38B has a stop ring 74B the same as stop ring 74D the same as stop ring 74B of container 32A of system 73 described above.

Another system 76 illustrated in FIGS. 12, 13, 14, and 15 include a rigid canister 14 containing body waste fluids 12 in storage volume 16 and covered by a canister lid 24C having an inlet port 26, a vacuum port 28, and an aperture 30C analogous to canister lid 24 with its ports 26 and 28 and aperture 30 of system 10. A container 78 having a continuous generally upright wall 80 configured as a cylinder and opposed upper and lower walls 82 and 84, respectively, that together define a sealed chamber 86 holding xerogel composition 42. Container 78 is sealably positioned in aperture 30C secured to lid 24C by sealing ring 81. Chamber 86 has an exit port 88 with lower wall 84 being removably mounted to cylindrical wall at exit port 88. A release device 90 mounted to container 78 includes lower wall 84 being a release head configured as a cone slidably mounted in chamber 86 and a vertical plunger rod 94 connected to the conical axis of lower wall release head 84 and slidably extending through upper wall 82 to a top end 95 spaced at a distance above upper wall 82. Conical lower wall release head 84 has an O-ring 96 mounted about its circumference so as to seal chamber 86. A plunger rod cap 98 at top end 95 of plunger rod 94 provides a surface for manual operation of plunger rod 94. A plastic peelable stop ring 99 is mounted around plunger rod 94 between upper wall 82 and cap 98; stop ring 99 prevents accidental movement of plunger rod 94. Prior to activation of plunger rod 94, stop ring 99 is peeled away from plunger rod by pulling from a vertical slit (not shown) in stop ring 99 in a manner known in the art. Plunger rod 94 is for moving lower wall release head 84 between an inactive position and an activated position, the inactive position being when lower wall release head 84 is located at exit port 88, and the activated position being when lower wall release head 84 is moved to a position below exit port 88, so that xerogel composition 42 is released from chamber 86 for downward movement into storage volume 16 of canister 14 for mixture therein with body waste fluids 12 resulting in the formation of a solidified mixture, or insoluble gel, 48 in storage volume 16.

Figure 16:
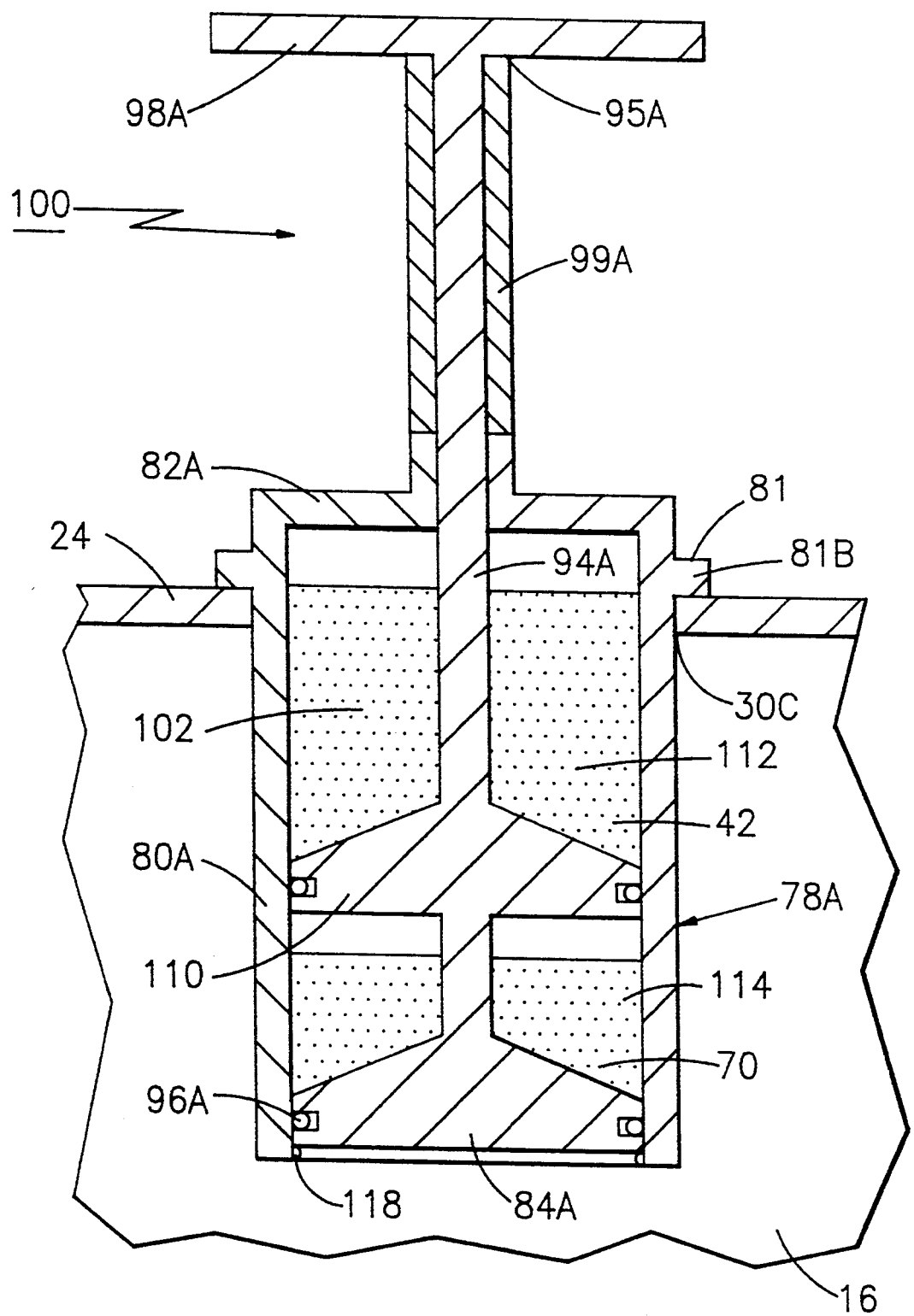
FIG. 16 is a fragmented sectional view of a xerogel container analogous to the xerogel container shown in FIG. 11 with the container holding both xerogel powder and a disinfectant with the plunger in an inactive mode.
Figure 17:
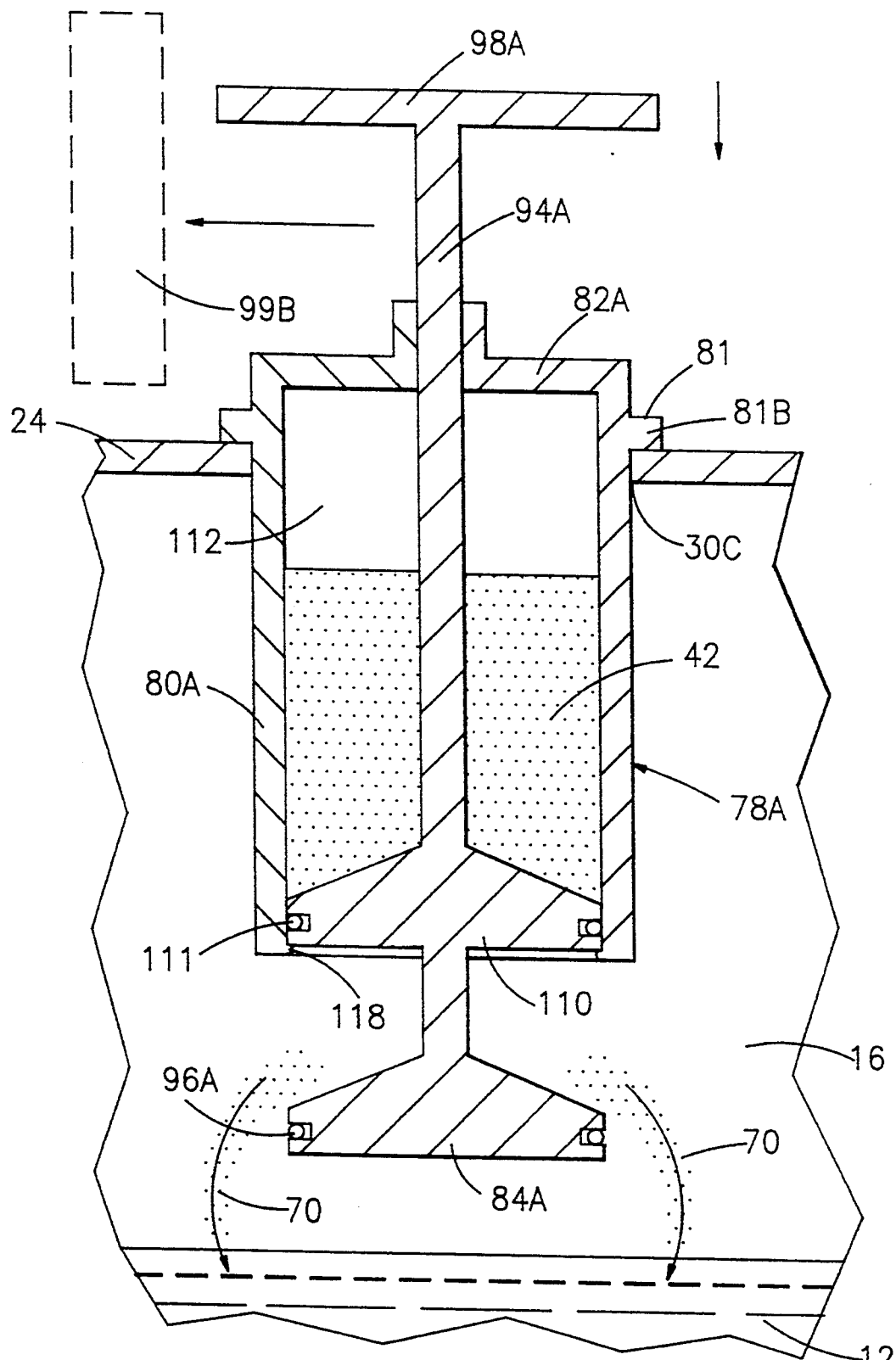
FIG. 17 is a fragmented sectional view analogous to the view shown in FIG. 16 with the plunger in a partially activated mode.
Figure 18:
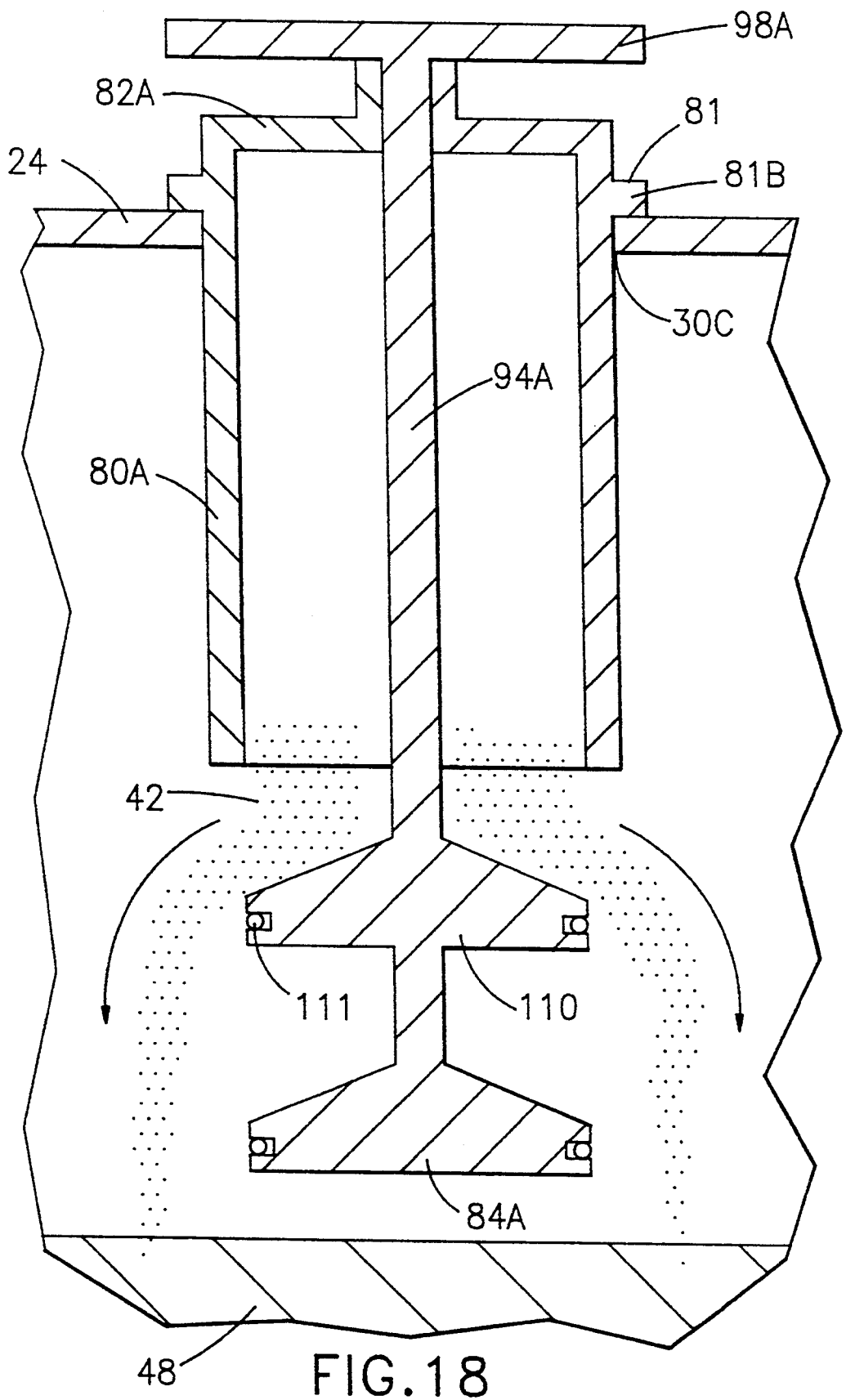
FIG. 18 is a fragmented sectional view analogous to the view shown in FIG. 17 with the plunger in a fully activated mode.

FIGS. 16, 17, and 18 illustrate a system 100 analogous to system 76 including a canister 14 having canister lid 24D having an inlet port 26, a vacuum port 28, and an aperture 30D analogous to lid 24 with its ports 26 and 28 and aperture 30 described above in relation to system 10 and containing body waste fluids 12 in storage volume 16. A container 78A includes a continuous, cylindrical upright wall 80A configured as a cylinder and an upper wall 82A and an opposed, cone-shaped lower wall, or release head, 84A that together define a sealed chamber 86A. Container 78A is sealably positioned in aperture 30D. Chamber 86A has an exit port 88A with lower wall 84A being removably mounted to cylindrical wall 80A at exit port 88A. A release device 102 mounted to container 78A includes a release head 84A and a vertical plunger rod 106 connected to the conical axis of release head 84A and slidably extending through upper wall 82A to a top end 107 spaced above upper wall 82A. Conical release head 84A has an O-ring 96A mounted about its circumference so as to seal chamber 86A. A plunger rod cap 108 at top end 107 of plunger rod 106 provides a surface for manual operation of plunger rod 94A.

System 100 includes a movable intermediate sealing wall 110 which when system 100 is in an inactive position is located within chamber 86A between and lateral to upper and lower chamber walls 82A and 84A forming from chamber 86A upper and lower compartments 112 and 114, respectively. Upper compartment 112 contains xerogel powder composition 42 and lower compartment 114 contains at least one disinfectant 70 in the form of a powder. Plunger rod 106 is connected with said intermediate release head 110 at the axis of its cone. Plunger rod 106 is for moving release head 104 and intermediate release head 110 from an inactive position to a semiactivated position and then to an activated position. The inactive position is when intermediate release head 110 is located at exit port 88A; the semiactivated position is when intermediate release head 110 is positioned below exit port 88A and intermediate release head 110 is positioned in alignment with exit port 88A wherein disinfectant 70 is released from lower compartment 114 for movement into storage volume 16 of canister 14 for mixture therein with body waste fluids 12 resulting in the destruction, or at least deactivation of body waste fluids 12 in storage volume 14 and intermediate release head 110 is positioned at exit port 88A; and the activated position is when release head 104 has been moved below exit port 88A wherein xerogel composition 42 is released from upper compartment 112 into storage volume 14 for mixture therein with the sterilized body waste fluids 12 resulting in the formation of a solidified mixture 48 in storage volume 14.

In both systems 76 and 100 removable locking strip 116 and 116A connected to plunger rods 94 and 106, respectively, between upper walls 82 and 82A and caps 98 and 98A, respectively, for maintaining plunger rods 76 and 100 at the respective distances between upper walls 82 and 82A and upper walls 82 and 82A, respectively, until manually removed in preparation for activation of plunger rods 94 and 106. Locking strip 116 is separated at a vertical line 118 and is preferably made of a thin resilient plastic.

Containers 78 and 78A of systems 76 and 100 can be independent of lids 24 and mountable to lids 24 as shown and described analogous to containers 32 and 32A of systems 76 and 100. In such independent systems a ring stop member 81 shown in FIGS. 13-18 is integral with container walls 34 and 34A. Containers 78 or 78A are mountable into pre-existing drainage ports 30C shown in FIGS. 13-18 defined in lids 24 after removal of their drainage port caps (not shown). Container walls 80 and 80A can be tapered for press or friction fit into drainage ports 30C.

Figure 23:
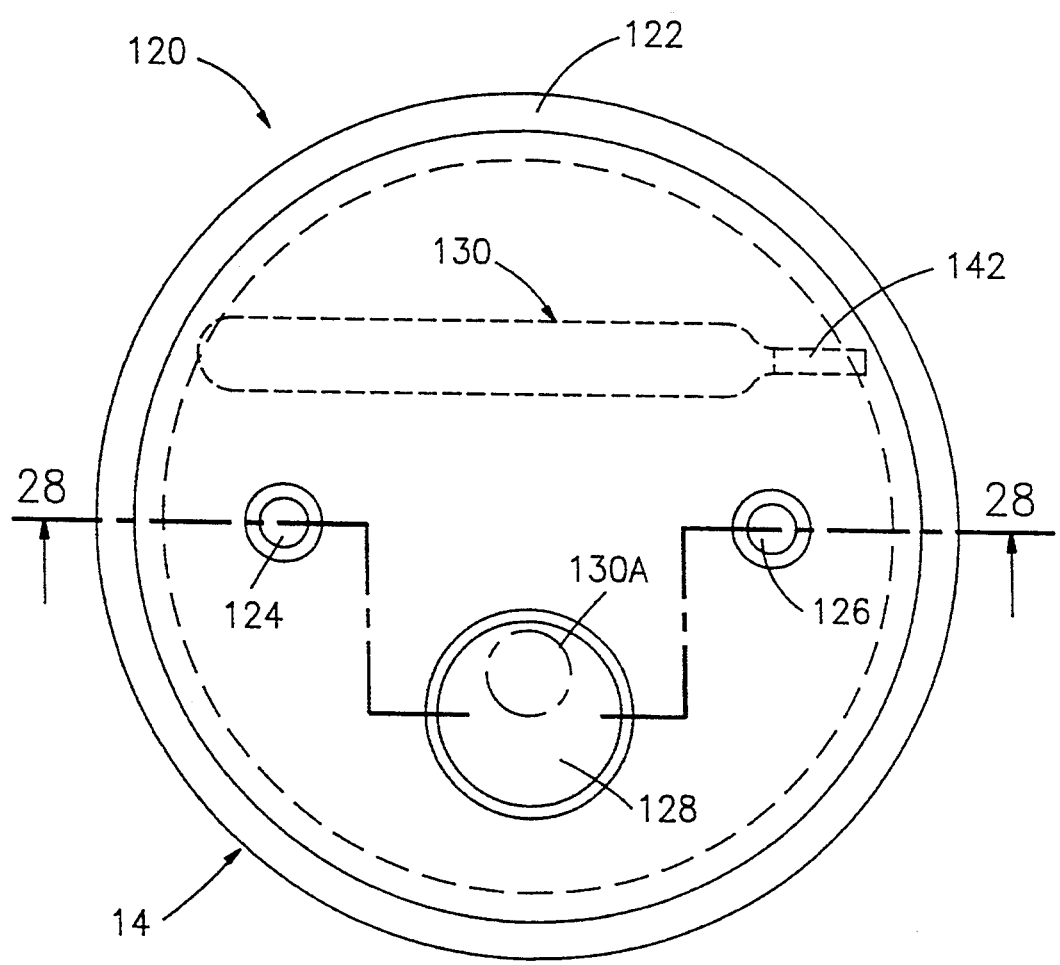
FIG. 23 is a top view of the canister and canister lid with the container shown in FIGS. 19-22 positioned in the storage volume after having been inserted into the canister through the canister lid as indicated in phantom line.
Figure 24:
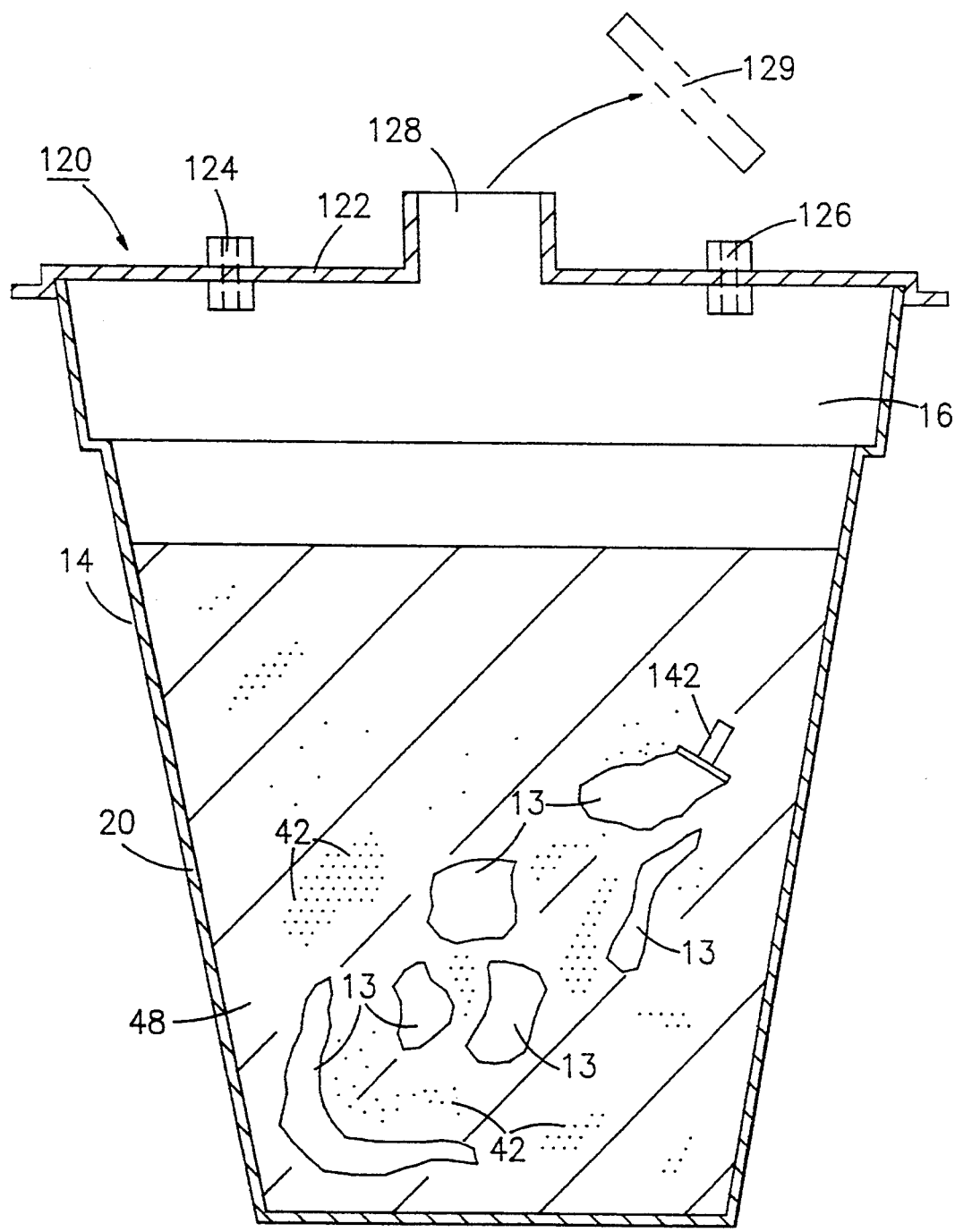
FIG. 24 is a sectional view taken through line 23—23 of FIG. 23.
Figure 25:
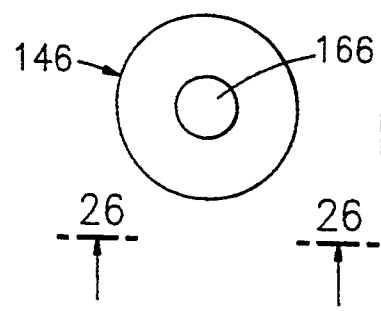
FIG. 25 is a top view of another body waste fluids solidification system similar to that shown in FIGS. 19-25 with the addition of an outer wall around the container.
Figure 27:
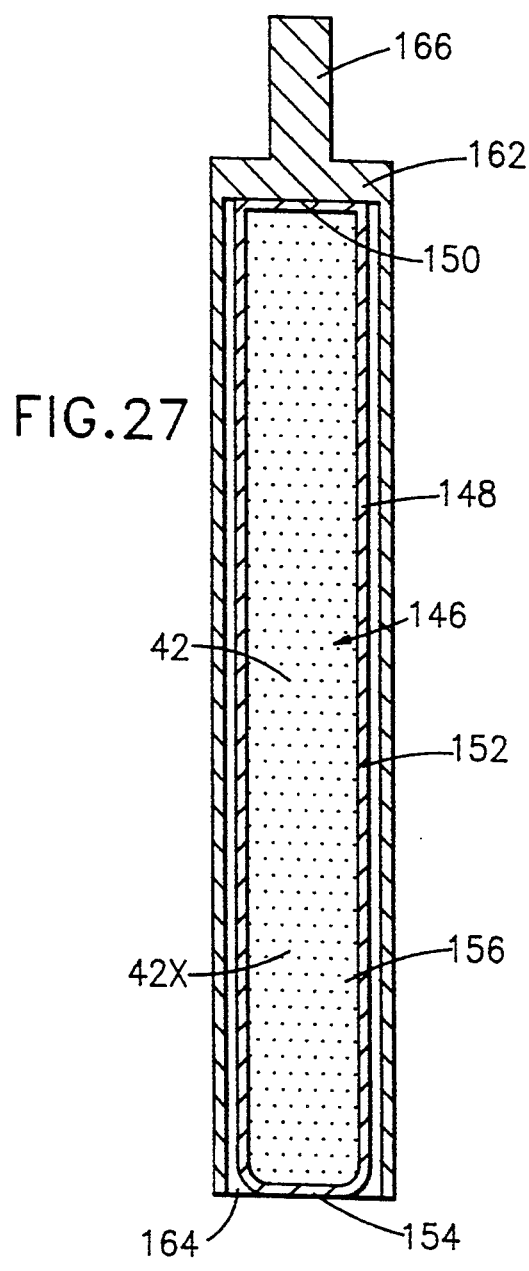
FIG. 27 is a sectional side view taken through line 27—27 in FIG. 26.
Figure 26:
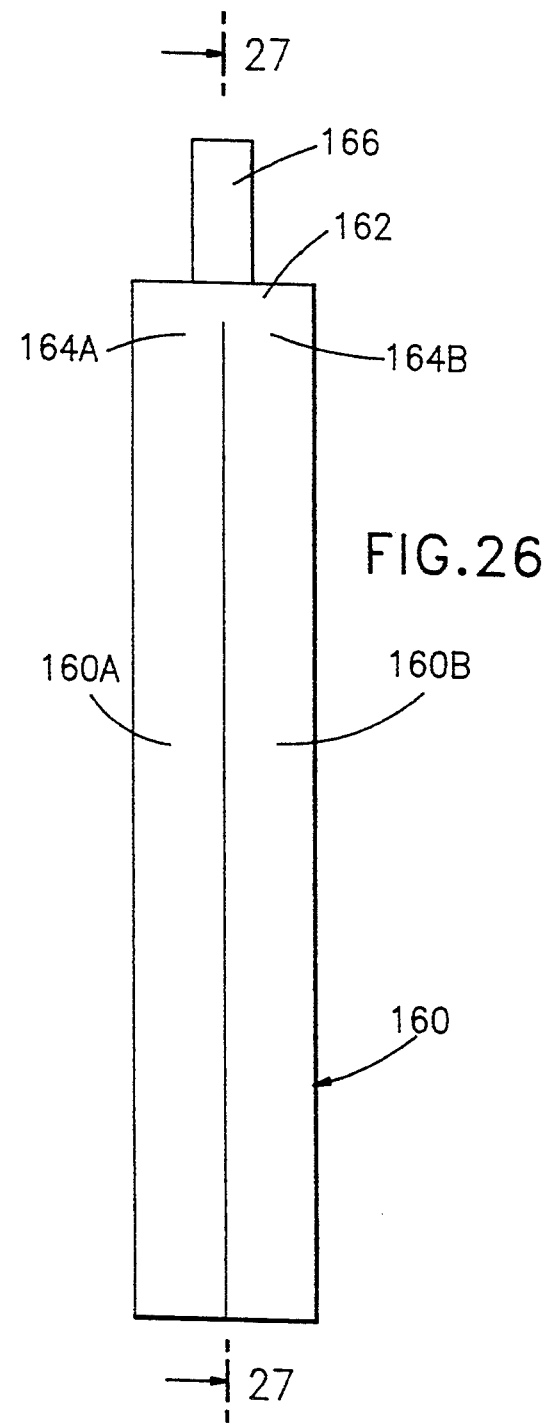
FIG. 26 is an elevational view taken though line 25—25 in FIG. 24.
Figure 28:
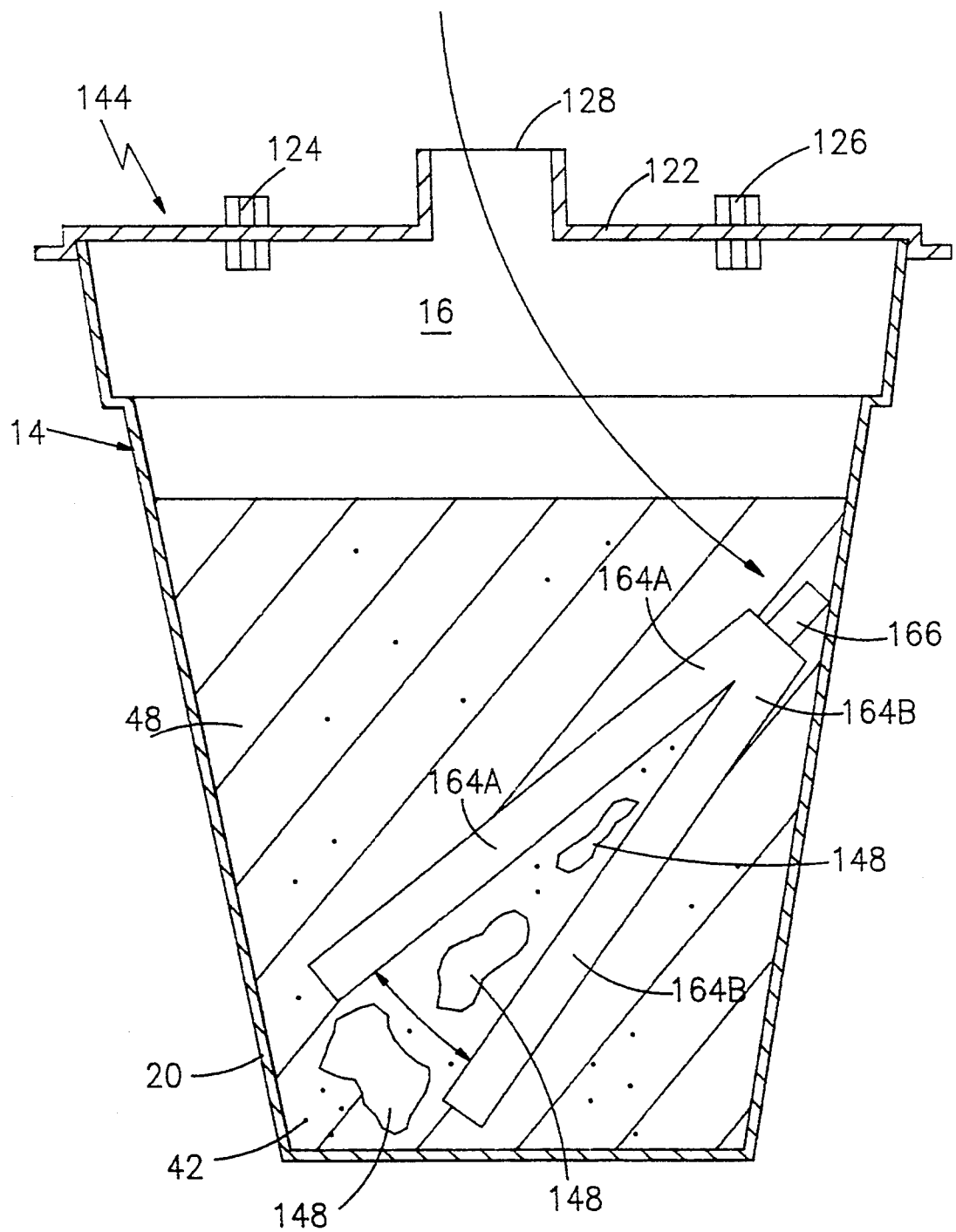
FIG. 28 is a sectional view showing the container with outer wall of FIGS. 25-27 in a canister analogous to the canister shown in FIGS. 23 and 24 with the xerogel composition escaping into contact with the body waste fluids.

FIGS. 19, 20, 21, 22, 23, 24, and 25 illustrate a system 120 for preparation for disposal of non-gaseous body waste fluids 12 collected in the rigid medical canister, or canister, 14 illustrated in FIGS. 1-4. As particularly shown in FIGS. 23 and 24, canister 14 has a canister lid 122 which defines an inlet port 124, a vacuum port 126, and a drainage port 128 opening to storage volume 12 in which body waste fluids 12 are held. A drainage port cap 129 is shown in phantom line in FIG. 24 in the removed position. An elongated container 130 having a continuous wall 132 including a top wall 134, a generally cylindrical side wall 136, and a bottom wall 138 opposed to top wall 134 which together define a chamber 140 in which xerogel composition 42 is held. A plastic grip 142 is attached to top wall 134. A release component comprises continuous wall 132 being made of a liquid absorbent material such as paper which also passes liquid which is made frangible by body waste fluids 12. Drainage port 128 has a cross-sectional area and configuration and container 130 has a cross-sectional area and configuration such that container 130 can be passed through drainage port 128 into storage volume 16. When container 130 is placed into storage volume 16 through drainage port 128 as indicated in FIG. 23 in phantom line as container 130A, the frangible paper of continuous wall 132 allows passage of body waste fluids 12 into chamber 140 into contact with part of xerogel composition 42 which thereupon absorbs some of body waste fluids 12 and expands as a mixture in chamber 140. As indicated in FIG. 24, where container 130 is shown within storage volume 16, the frangible paper of continuous wall 132, which has a strength less than the force placed upon it by the mixture in chamber 140 which expands as xerogel composition 42 absorbs body waste fluids 12, breaks, whereupon the remainder of xerogel composition 42 passes from chamber 140 into contact with and mixes with body waste fluids 12 in storage volume 16 so as to immobilize body waste fluids 12 therein into a solidified mixture in storage volume 16.

FIGS. 25, 26, 27, and 28 illustrate another system 144 analogous to system 120 including an elongated container 146 which is the same as container 130 and having a continuous wall 148 including a top wall 150, a generally cylindrical side wall 152, and a bottom wall 154 opposed to top wall 150 which together define a chamber 156 in which body waste fluids 12 are held. A release component includes continuous wall 148 being made of a liquid absorbent material such as paper which also passes liquid which is made frangible by body waste fluids 12. System 144 further includes a cylindrical outer wall 160 made of a rigid, flexible, non-porous plastic material and is secured to a plastic support 162 attached to top wall 150. Outer wall 160 surrounds and slightly spaced from side wall 152 defining a cylindrical passage 164 between side wall 152 and outer wall 160. Outer wall 160 includes a pair of opposed semicylindrical outer wall portions 160A and 160B, which are integrally joined to support 162 as hinges 164A and 164B, respectively. When body waste fluids 12 enter passage at bottom wall 154, body waste fluids 12 gradually come into contact with and pass through side wall 152 and come into contact with xerogel composition 42 in container 146, that is, in chamber 156, forming a mixture in chamber 146. The mixture expands and breaks portions of continuous wall 148 thus forcing outer wall portions 160A and 160B away from side wall 152 with contact remaining at hinges 164A and 164B. Thus, system 144 limits the movement of and gradually passes body waste fluids 12 to continuous wall 148 when system 144 with container 146 is positioned in storage volume 16. The remainder of xerogel composition 42 passes from chamber 156 into contact with and mixes with body waste fluids 12 in storage volume 16 so as to immobilize body waste fluids 12 therein into a solidified mixture, or gel, 48 in storage volume 16. A grip or handle 166 is connected to the top of support 162.

FIGS. 29, 30, 31, and 32 illustrate a system 168 for preparation for disposal of non-gaseous body waste fluids 12 collected in a rigid medical canister analogous to canister, 14 and canister lid 122 illustrated in FIGS. 23 and 24. A container 170 includes a continuous wall 172 enclosing xerogel composition 42 within container 170. Continuous wall 172 includes a flat wall 174, which is made of a liquid absorbent and liquid porous material made frangible by the liquid such as paper. Continuous wall 172 further includes a stepped plastic wall 176 having integral transverse flanges 177A and 177B to which flaps 174A and 174B integral with flat wall 174 are attached. Stepped wall 176 is opposed to flat wall 174. Continuous wall 172 further includes a pair of opposed plastic planar side walls 178A and 178B connected to transverse plastic flanges 177A and 177B and to stepped plastic wall 176. Stepped plastic wall 176 includes three downwardly and outwardly extending connecting wall portions 180A, 180B, and 180C joined by three downwardly and inwardly sloped wall portions 182A, 182B, and 182C. Sloped portions 180A-C, 182A-C, side walls 178A and 178B, and flat wall 174 define a chamber comprising three joined compartments 184A, 184B, and 184C containing xerogel composition 42. A plastic handle 186 is integral with plastic stepped wall 176.

When container 170 is manually placed into storage volume 16 of canister 12 through drainage port 128 of canister lid 122, the frangible paper of continuous wall 172 allows passage of body waste fluids 12 into compartments 184A, 184B, and 184C into contact with part of xerogel composition 42 which thereupon absorbs some of body waste fluids 12 and expands as a mixture in compartments 184A, 184B, and 184C. The frangible paper of continuous wall 174, which has a strength less than the force placed upon it by the mixture in compartments 184A-C, breaks as xerogel composition 42 absorbs body waste fluids 12 expands, whereupon the remainder of xerogel composition 42 passes from compartments 184A-C into contact with and mixes with body waste fluids 12 in storage volume 16 so as to immobilize body waste fluids 12 therein into a solidified mixture, or gel, 48 in storage volume 16. The movement of xerogel 42 from compartments 184A-C is aided by downward slopes 182A, 182B, and 182C.

FIGS. 33, 34, 35 and 36 illustrate a system 188 analogous to system 168 for preparation for disposal of non-gaseous body waste fluids 12 collected in a rigid medical canister analogous to canister, 14 and canister lid 122 illustrated in FIGS. 23 and 24. A container 190 includes a continuous wall 192 enclosing xerogel composition 42 within container 190. Continuous wall 192 includes a flat wall 194, which is made of a liquid absorbent and liquid porous material made frangible by the liquid, such as paper. Continuous wall 192 further includes a stepped wall 196 made of plastic or other material impervious to the passage of fluids having transverse flanges 197A and 197B to which flaps 194A and 194B of flat wall 194 are attached. Stepped wall 196 is opposed to flat wall 194. Continuous wall 192 further includes a pair of opposed plastic planar side walls 198A and 198B connected to plastic flanges 197A and 197B and to stepped plastic wall 196. Stepped plastic wall 196 includes three horizontal wall portions 200A, 200B, and 2000C extending to flat wall 194 joined by three downwardly and inwardly sloped wall portions 202A, 202B, and 202C likewise extending to flat wall 194. Horizontal portions 200A-C, sloped portions 202A-C, side walls 198A and 198B, and flat wall 194 define three spaced apart sealed, individual chamber, or compartments, 204A, 204B, and 204C each containing xerogel composition 42. Stepped wall 196 further includes three horizontal connecting wall portions 206A, 206B, and 206C extending to flat wall 194 joined by three downwardly and inwardly sloped wall portions 208A, 208B, and 208C likewise extending to flat wall 194. Horizontal portions 206A-C, sloped portions 208A-C, side walls 198A and 198B, and flat wall 194 define three chambers, or compartments, 210A, 210B, and 210C each positioned immediately below compartments 204A, 204B, and 204C, respectively. Short connecting segments 212 flush with flat wall 194 seal compartments 204A-C and 210A-C from one another. A plastic handle 214 is integral with plastic stepped wall 196. Compartments 210A, 210B, and 210C each contain at least one disinfectant 70 as described above in relation to system 10.

As illustrated in FIG. 36, when container 190 is manually placed into storage volume 16 of canister 12 through drainage port 128 of canister lid 122, the frangible paper of flat wall 194 allows passage of body waste fluids 12 into xerogel compartments 204A-C into contact with part of xerogel composition 42 which thereupon absorbs some of body waste fluids 12 and expands as a mixture in xerogel compartments 204A-C. The frangible paper of flat wall 194, including both the portions of flat wall 194 overlying disinfectant compartments 210A-C as well as xerogel compartments 204A-C, which has a strength less than the force placed upon it by the expanding mixture in xerogel compartments 204A-C, breaks, whereupon the remainder of xerogel composition 42 passes from xerogel compartments 204A-C into contact with and mixes with body waste fluids 12 in storage volume 16 at generally the same time as disinfectant 70 escapes from compartments 214A-C so as to immobilize body waste fluids 12 therein into a solidified mixture, or gel, 48 in storage volume 16 at the same time as disinfectant 70 passes into body waste fluids 12 resulting in the simultaneous destruction or deactivation of infectious agents within body waste fluids 12. The movement of xerogel composition 42 from xerogel compartments 204A-C and disinfectant compartments 210A-C is aided by sloped wall portions 202A-C and 208A-C.

Figure 37:
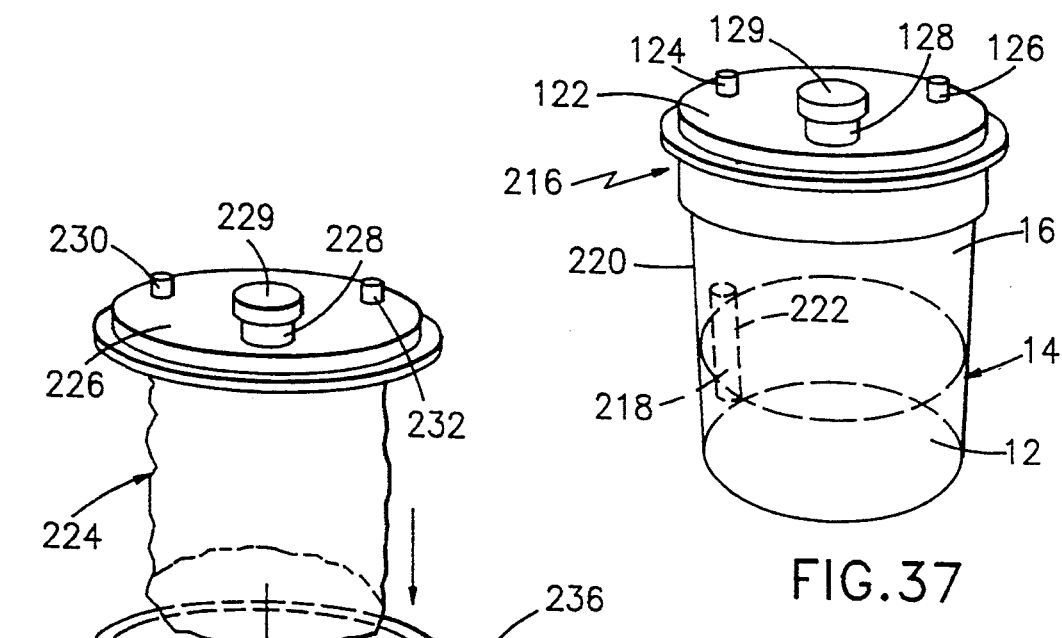
FIG. 37 is a perspective view of a canister with a container secured to the inner surface of the canister wall in the storage volume.

FIG. 37 illustrates a system 216 for preparation for disposal of non-gaseous body waste fluids 12 collected in a rigid medical canister 14 analogous to canister 14 and canister lid 122 illustrated in FIGS. 23 and 24. An elongated container 218 is secured to the inner surface of container cylindrical wall 220 in storage volume 16. Container 218 includes a continuous wall 222 including at least one portion of continuous wall 222 being made of a liquid absorbent material made frangible by body waste fluids 12. Container 218 represents any of the following containers: container 130 described in reference to system 120; container 146 of system 144; container 170 of system 168; and container 190 of system 188. The sequential occurrences are analogous to those described for the mentioned systems. Specifically, as body waste fluids 12 come into contact with the portion of continuous wall 222 made frangible by body waste fluids 12 that rise upwardly in a gradual manner and pass through that portion to admix with xerogel composition 42 within container 218, xerogel composition 42 absorbs the fluids and expands thus breaking the portion of continuous wall 222 made of frangible material in contact with the rising fluids so that xerogel composition diffuses into body waste fluids 12 and interacts with body waste fluids 12 so as to immobilize body waste fluids 12 into a solidified mixture (not shown) like solidified mixture, or gel, 48 shown previously in system 10.

Figure 38:
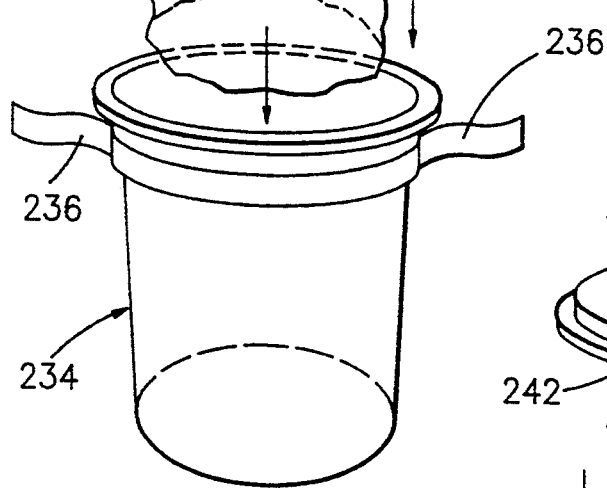
FIG. 38 is a perspective view of a medical vessel having a flexible plastic wall with an integral lid having a drainage port being inserted into a permanent hard-walled support container of the type mounted to a vacuum machine.

FIG. 38 illustrates a flexible-walled plastic collection vessel 224 with an integral lid 226, which is often used to collect body waste fluids 12 in contrast to the hard-walled canister 14 with removable canister lid 24 of system 10. Lid 226 has a drainage port 228 with a drainage port cap 229, a patient inlet port 230, and a vacuum port 232. Vessel 224 is in operation set into a medical hard-walled canister 234, which is secured by mounts 236 to a vacuum machine (not shown). When vessel 224 is full, it is lifted, along with lid 226, from canister 234 and disposed of in the manner described for the disposal of body fluid wastes earlier. Canister 234, being dry and uncontaminated, is retained. Container 130 described in reference to system 120; container 146 of system 144; container 170 of system 168; and container 190 of system 188 can all be also used for flexible-walled collection vessel 224 by placement of the named containers into vessel 224 through drainage port 228. In addition, container 32A of system 73 illustrated in FIGS. 9 and 10 and container 32B illustrated in FIG. 11 of system 75 illustrated in FIG. 11 are also insertable into storage volume 16 through drainage port 228. In the just-mentioned containers, when insertion is made, body waste fluids 12 are immobilized in the form of solidified mixture, or gel, 48 in the manner described. In addition, where present, disinfectant 70 also destroys or deactivates infectious agents in body waste fluids 12.

Figure 39:
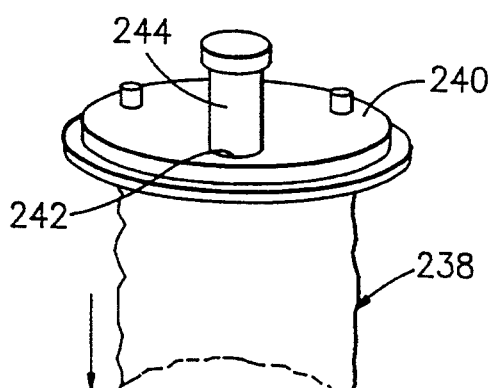
FIG. 39 is a perspective view of a medical vessel having a flexible plastic wall with an integral lid having a container holding xerogel or xerogel and disinfectant permanently affixed to the lid and occupying an aperture in the lid.

FIG. 39 also illustrates a flexible-walled plastic collection vessel 238 analogous to vessel 224 used to collect body waste fluids 12. Vessel 238 has an integral lid 240 which has an aperture 242 through which is sealably mounted a container 244 analogous to container 32 of system 10, container 32A of system 62, container 78 of system 76, and container 78A of system 100. Vessel 238 is in operation set into a medical hard-walled canister 234, which is secured by mounts 236 to a vacuum machine (not shown). When vessel 238 is full, container 244 is manually operated in the manner described for systems 10, 62, 76, and 100. After the immobilization of body waste fluids 12 in the form of solidified mixture, or gel, 48, vessel 238 is lifted along with its lid 240 and container 244 from canister 23 and disposed of in the manner described earlier for the disposal of body waste fluids where body waste fluids 12 are immobilized in the form of solidified mixture, or gel, 48.

Xerogel composition 42 specified in each of the several systems set forth above comprises at least one water-insoluble hydrophilic polymer. Xerogel composition 42 is selected from the group comprising partially hydrolyzed poly(vinyl acetate), cross-linked poly(vinyl alcohol), cross-linked hydroxyalkyl acrylates and methacrylates, polymers and copolymers of ethylene oxide and polymers and copolymers acrylamide. Xerogel composition 42 is further selected from the group comprising acrylonitrile -acrylamide copolymers, poly(ethylene oxide) polymers and copolymers, cellulose - starch - acrylates and ground corn husks.

Disinfectant 70 specified in systems 62, 100, and 178 set forth above comprises at least one disinfectant to destroy infectious substances within the body waste fluids 12 upon interaction therewith. The composition of disinfectant 70 is selected from the group comprising quarternary ammonium compounds, alcohols, phenols, aldehydes and ketones, chlorine releasing agents, iodine releasing agents, nonionic, cationic and anionic detergents, oxidants, phenols, phenolic aldehydes, hexachlorophene chlorhexidine gluconate, precursors for the above, and the like, and salts and mixtures thereof.

Disinfectant 70 is also selected from the group comprising germicides such as bacteriocides, bacteriostats, fungicides, and the like, to destroyed and, if desired, disinfected infectious components of body waste fluids 12.

Xerogel composition 42 and disinfectant 70 may be premixed and the admixture subsequently added to body waste fluids 12, specifically for the systems 10, 73, 76, 120, 144, and 168 wherein the chambers for those systems are described as containing xerogel composition 42. Such admixtures of xerogel composition 42 and disinfectant 70 are indicated by numeral 42X and phantom lead line in FIGS. 2, 9, 13, 21, 27, and 31.

All connections between the containers and the lids of systems 10, 62, 73, 76, 100, and 216 can be by threaded connections or by bayonet connections known in the art, neither of which connections are specifically shown.

Although the present invention has been described in some detail by way of illustration and example for purposes of clarity and understanding, it will, of course, be understood that various changes and modifications may be made in the form, details, and arrangements of the parts without departing from the scope of the invention set forth in the following claims.

What is claimed is:

1. A body waste fluid solidification device for facilitating disposal, comprising:
   a lid having a waste inlet line;
   a substantially rigid, self standing medical collection vessel, having a rim, said vessel for collecting body waste fluids which flow via said waste inlet line in said lid for collection in said medical collection vessel, and said lid closing off the rim of said medical collection vessel for sealing same from ambient conditions; container means separate from said medical collection vessel of hollowed cylindrical shape having a chamber substantially filled with a hydrophilic xerogel composition;
   said container means further having a chamber separating means for separating at least one disinfectant from said hydrophilic xerogel, said chamber separating means formed by at least a continuous side wall and an upper wall flexibly and integrally connected to said continuous side wall;
   said container means mounted in an opening on said lid; and
   a pressure responsive plunger release means operatively associated with said container means for sequentially dispensing when activated by pressure said at least one disinfectant and then subsequently said hydrophilic xerogel composition when desired from said container means into said medical collection vessel for contacting said body waste fluids collected in said medical collection vessel, for said initial sterilizing or disinfecting and then subsequently for solidifying said fluids, as desired, thereby minimizing the hazards of handling the solidified waste fluids collected in said substantially rigid, self standing medical collection vessel.

2. The device according to claim 1, wherein said disinfectant is in the form of a free-flowing powder.

3. The device according to claim 1, wherein said container means includes a container having a sealed chamber, said chamber having upper and lower compartments, said upper compartment being for holding said xerogel composition and said lower compartment being for holding said at least one disinfectant.

4. The device according to claim 3, wherein said release means allows said at least one disinfectant to exit from said lower compartment prior to said exit of said xerogel composition, wherein said at least one disinfectant mixes with the body waste fluids before said xerogel composition causes solidification of the body waste fluids.

5. The device according to claim 1, wherein the vessel defines a storage volume for the body waste fluids,
said container means further including a lower wall opposed to said upper wall and said continuous side wall is generally upright wall, said continuous generally upright wall, said upper and lower walls defining a chamber of said camber separating means, said lower wall of said chamber having an exit port opening to said storage volume, said lower wall being removably mounted to said continuous wall at said exit port.

6. The device according to claim 5, wherein said plunger-release means includes a punch head slidably mounted in said chamber and a generally vertical connecting means for joining said upper wall with said punch head, said upper wall, said generally vertical connecting means and said punch head being movable for a short distance from an inactive position to an activated position, with said inactive position being when said punch head is spaced above said lower wall, and said activated position being when said punch head is positioned below said exit port after having punched said lower wall, wherein said at least one disinfectant and then said hydrophilic xerogel composition are sequentially released in a controlled manner from said chamber for movement into the storage volume of the vessel for mixture therein with the body waste fluids.

7. The device according to claim 6, wherein said chamber is configured as a cylinder having a general vertical axis and said punch head is configured as an interior cylindrical wall slidably mounted within said chamber, and said connecting means includes a generally vertical connecting rod positioned at said vertical axis of said cylinder and having upper and lower ends, said lower end being spaced above said punch head, said upper end being flexibly connected to said upper wall, said connecting means further including a plurality of equally spaced support rods connected to and extending downwardly between said lower end of said connecting rod and said punch head, said chamber including areas above and below said support rods, wherein the portion of said xerogel powder positioned in said chamber above said punch head passes downwardly between said plurality of support rods when said punch head is moved to said activated position.

8. The device according to claim 7, wherein said removable lower wall is thin and is made of a penetrable material and said punch head includes a plurality of downwardly directed piercing tips located around said interior cylindrical wall of said punch head, wherein when said punch head is moved from said inactive to said activated position, said piercing tips penetrate said lower wall so as to aid in the removal of said lower wall from sealable connection with said container means.

9. The device according to claim 8, wherein said lid of said vessel has an aperture, said container means being sealably mounted to said lid and being positioned within said aperture.

10. The device according to claim 8, wherein said lid of said vessel has a port, said container means being mounted to said lid and being positioned within said port.

11. The device according to claim 8, further including a removable intermediate sealing wall which when the system is in said inactive position is located within said chamber between and lateral to said upper and lower walls forming from said chamber upper and lower compartments, wherein said upper compartment contains said xerogel powder, and said lower compartment contains said at least one disinfectant.

12. The device according to claim 11, wherein said upper wall, said connecting means, and said punch head are movable from said inactive position to a semiactivated position and then movable to said activated position; said inactive position being when said punch head is located above said exit port; said semiactivated position being when said punch head is positioned immediately above said removable intermediate sealing wall after having caused said removable lower wall to be moved from connection with said container means via pressure from said punch head causing said intermediate wall to be moved to said exit port via pressure exerted by said xerogel composition, wherein said at least one disinfectant is released from said lower compartment for movement into the storage volume of the vessel for mixture therein with the body waste fluids resulting in the substantial destruction, or at least deactivation of infectious agents within the body waste fluids in the storage volume; and said activated position being when said punch head has been moved for positioning at said exit port after having punched said said removable intermediate wall from connection with said container means into the storage volume of the vessel, wherein said xerogel composition is released from said upper compartment into the storage volume of the vessel for mixture therein with the sterilized body waste fluids resulting in the formation of a solidified mixture in the storage volume.

13. The device according to claim 12, further including supporting locking means integral with said container means at said exit port for holding said lower wall in position at said exit port when the system is in said inactive position and also for holding said intermediate wall in position at said exit port when the system is in said semiactivated position.

14. The device according to claim 11, wherein said lid of said vessel has an aperture, said container means being fixed to said lid and being positioned within said aperture.

15. The device according to claim 11, wherein said lid of skid vessel has a port, said container means being mounted to said lid and being positioned within said port.

16. The device according to claim 5, wherein said plunger release means includes a sealed release head slidably and sealably mounted in said chamber and plunger means connected to said release head and slidably extending through said upper wall to a position spaced above said upper wall accessible for manual operation, said plunger means being for moving said release head between an inactive position and an activated position, said inactive position being when said release head is located at said exit port, and said activated position being when-said release head is positioned below said exit port.

17. The device according to claim 16, wherein said chamber is configured as a cylinder having a general vertical axis and said release head is configured as a cone slidably mounted within said chamber with the plunger means aligned with the axis of the cone.

18. The device according to claim 16, wherein said lid of said vessel has an aperture, said container means being fixed to said lid and positioned within said aperture.

19. The device according to claim 16, wherein said lid of said vessel has a drainage port, said container means being mounted to said lid positioned within said drainage port.

20. The device according to claim 17, further including an intermediate release head which when said system is in said inactive position is located within said chamber forming from said chamber upper and lower compartments, wherein said upper compartment contains said xerogel powder, and said lower compartment contains at least one disinfectant.

21. The device according to claim 20, wherein said intermediate release head is configured as a cone with said plunger means being connected with said intermediate release head at the axis of said cone.

22. The device according to claim 20, wherein said plunger means is for moving said release head and said intermediate release head from said inactive position to a semiactivated position and then to said activated position; said inactive position being when said release head is located at said exit port; said semiactivated position being when said release head is positioned below said exit port and said intermediate release head is positioned in alignment with said exit port wherein said at least one disinfectant is released from a lower compartment for movement into the storage volume of the vessel for mixture therein with the body waste fluids resulting in the substantial destruction, or at least deactivation of infectious agents within the body waste fluids in the storage volume, and said intermediate release head is positioned at said exit port; and said activated position being when said release head has been moved below said exit port.

23. The device according to claim 22, wherein said plunger means includes a plunger rod slidably mounted through said upper wall and having top and bottom ends, said top end being located above said upper wall and said lower end being connected with said release head.

24. The device according to claim 23, wherein said plunger rod includes a plunger head at said top end, said plunger head being spaced from said upper wall at a distance, and removable locking means connected to said plunger rod for maintaining said plunger rod at said distance until manually removed in preparation for activation of said plunger rod.

25. The device according to claim 22, wherein said lid of said vessel has an aperture, said container means being fixed to said lid and positioned within said aperture.

26. The device according to claim 22, wherein said lid of said vessel has a drainage port, said container means being mounted to said lid positioned within said drainage port.

27. The device according to claim 1, wherein said xerogel composition is selected from the group consisting of partially hydrolyzed poly(vinyl acetate), cross-linked poly(vinyl alcohol), cross-linked hydroxyalkyl acrylates and methacrylates, polymers and copolymers of ethylene oxide and polymers and copolymers acrylamide.

28. The device according to claim 1, wherein said xerogel composition is selected from the group consisting of acrylonitrile - acrylamide copolymers, poly(ethylene oxide) polymers and copolymers, cellulose - starch - acrylates and ground corn husks.

29. The device according to claim 1, wherein said disinfectant is selected from the group consisting of quarternary ammonium compounds, alcohols, phenols, aldehydes and ketones, chlorine releasing agents, iodine releasing agents, nonionic, cationic and anionic detergents, oxidants, phenols, phenolic aldehydes, hexachlorophene chlorhexidine gluconate, precursors for the above, and salts and mixtures thereof.

30. The device according to claim 1, wherein said disinfectant is selected from the group consisting of germicides such as bacteriocides, bacteriostats, fungicides.

31. The device according to claim 27, wherein said xerogel composition and said disinfectant are in admixture.

* * * * *